US011530300B2

(12) United States Patent
Netravali et al.

(10) Patent No.: US 11,530,300 B2
(45) Date of Patent: *Dec. 20, 2022

(54) RESIDUAL SOY FLOUR SUGARS AS CROSSLINKERS FOR ENHANCING MECHANICAL PERFORMANCE OF PROTEIN FIBERS

(71) Applicant: CORNELL UNIVERSITY, Ithaca, NY (US)

(72) Inventors: Anil N. Netravali, Ithaca, NY (US); Namrata V. Patil, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 187 days.

This patent is subject to a terminal disclaimer.

(21) Appl. No.: 16/813,694

(22) Filed: Mar. 9, 2020

(65) Prior Publication Data

US 2020/0207924 A1 Jul. 2, 2020

Related U.S. Application Data

(63) Continuation-in-part of application No. 15/307,828, filed as application No. PCT/US2015/028959 on May 1, 2015, now Pat. No. 11,019,902.

(Continued)

(51) Int. Cl.
*A61K 9/00* (2006.01)
*C08H 1/06* (2006.01)
(Continued)

(52) U.S. Cl.
CPC ............ *C08H 1/06* (2013.01); *A45D 7/06* (2013.01); *C08H 1/02* (2013.01); *D06M 10/08* (2013.01);
(Continued)

(58) Field of Classification Search
CPC ........................................... C08H 1/06
See application file for complete search history.

(56) References Cited

U.S. PATENT DOCUMENTS 3,051,544 A * 8/1962 Von Bergen ........... D06C 23/00
8/127.6
4,272,470 A    6/1981 Hsu et al.
(Continued)

FOREIGN PATENT DOCUMENTS

CN    101544705 B    9/2009
KR    1020130060594 A    6/2013
(Continued)

OTHER PUBLICATIONS

US 8,679,466 B2, 03/2014, Paul et al. (withdrawn)
(Continued)

*Primary Examiner* — Paul W Dickinson
(74) *Attorney, Agent, or Firm* — FisherBroyles, LLP; Andrew K. Gonsalves, Esq.

(57) ABSTRACT

Disclosed is a method of crosslinking protein fibers, including wool fibers, by (i) providing a crosslinking agent including an oxidized sugar mixture having a plurality of different oxidized sugars of different molecular lengths and having at least two aldehyde groups (e.g., oxidized soy flour sugars); and (ii) infiltrating a plurality of non-crosslinked protein fibers with the crosslinking agent under conditions effective to cause protein molecules contained in the non-crosslinked protein fibers to become crosslinked. This method yields a population of crosslinked protein fibers, where the protein molecules of the non-crosslinked protein fibers include amine groups that react with the aldehyde groups of the oxidized sugars to achieve the crosslinking of the protein molecules to yield the crosslinked protein fibers.

23 Claims, 24 Drawing Sheets

Related U.S. Application Data

(60) Provisional application No. 62/815,279, filed on Mar. 7, 2019, provisional application No. 61/987,328, filed on May 1, 2014.

(51) Int. Cl.
*C08H 1/02* (2006.01)
*D06M 13/123* (2006.01)
*D06M 10/08* (2006.01)
*D06M 13/188* (2006.01)
*A45D 7/06* (2006.01)

(52) U.S. Cl.
CPC ........ *D06M 13/123* (2013.01); *D06M 13/188* (2013.01)

(56) References Cited

U.S. PATENT DOCUMENTS

| | | | |
|---|---|---|---|
| 5,308,641 | A | 5/1994 | Cahalan et al. |
| 5,972,385 | A * | 10/1999 | Liu .................. A61L 27/24 424/486 |
| 7,988,954 | B2 | 8/2011 | Chandra et al. |
| 8,182,798 | B2 | 5/2012 | Paul |
| 8,187,582 | B2 | 5/2012 | Pye et al. |
| 8,192,728 | B2 | 6/2012 | Paul |
| 8,273,335 | B2 | 9/2012 | Pye et al. |
| 8,580,237 | B2 | 11/2013 | Paul |
| 2001/0034315 | A1 | 10/2001 | Grainger et al. |
| 2003/0029588 | A1 | 2/2003 | Cui |
| 2004/0023836 | A1 | 2/2004 | Moorfield et al. |
| 2006/0276370 | A1 | 12/2006 | Zhang et al. |
| 2010/0135946 | A1 | 6/2010 | Paul |
| 2010/0172855 | A1 | 7/2010 | Paul |
| 2010/0196303 | A1 | 8/2010 | Paul |
| 2011/0044925 | A1 | 2/2011 | Pye et al. |
| 2011/0120489 | A1 | 5/2011 | Pye et al. |
| 2012/0034180 | A1 | 2/2012 | Paul et al. |
| 2012/0093755 | A1 * | 4/2012 | Humphreys ............ A61K 8/64 424/70.14 |
| 2013/0071344 | A1 | 3/2013 | Amin et al. |
| 2013/0084260 | A1 | 4/2013 | Amin et al. |
| 2013/0142749 | A1 | 6/2013 | Paul et al. |
| 2013/0344006 | A1 | 12/2013 | Akinpelu et al. |
| 2013/0344017 | A1 | 12/2013 | Chandra et al. |
| 2013/0344020 | A1 | 12/2013 | Akinpelu et al. |
| 2018/0079832 | A1 * | 3/2018 | Paullin ................. C08B 37/00 |

FOREIGN PATENT DOCUMENTS

| | | |
|---|---|---|
| WO | 2001031112 A2 | 5/2001 |
| WO | 2006090119 A1 | 8/2006 |
| WO | 2008012732 A2 | 1/2008 |
| WO | 2008110399 A1 | 9/2008 |
| WO | 2009118253 A2 | 10/2009 |
| WO | 2012107367 A1 | 8/2012 |
| WO | 2013064597 A2 | 5/2013 |
| WO | 2013076061 A2 | 5/2013 |
| WO | 2014089578 A1 | 6/2014 |
| WO | 2014135433 A2 | 9/2014 |
| WO | 2015054018 A1 | 4/2015 |
| WO | 2015094757 A1 | 6/2015 |
| WO | 2015094760 A1 | 6/2015 |
| WO | 2015094787 A1 | 6/2015 |
| WO | 2015094838 A1 | 6/2015 |

OTHER PUBLICATIONS

International Searching Authority, International Search Report and Written Opinion issued in counterpart International Application No. PCT/US2015/028959, dated Sep. 1, 2015.
European Patent Office, European Search Report issued in counterpart European Patent Application No. EP 15785561 dated Jan. 2, 2018.
Herrmann, K.W., "Hair Keratin Reaction, Penetration, and Swelling in Mercaptan Solutions," Transactions of the Faraday Society, 59:1663-1671 (1963).
Wong et al., "Mechanism of Hair Straightening," J. Soc. Cosmet. Chem., 45:347-352 (1994).
Velasco et al., "Hair Fiber Characteristics and Methods to Evaluate Hair Physical and Mechanical Properties," Brazilian J. Pharm. Sci., 45(1):153-162 (2009).
Dastidar et al., "A Soy Flour Based Thermoset Resin without the Use of Any External Crosslinker," Green Chem., 15:3243-3251 (2013).
Inoue et al., "Structural Analysis of Human Hair in Aqueous Solutions Using Microbeam X-ray Diffraction," Research Frontiers, Spring 8, pp. 46-47 (2007).
Moss et al., Glossary of Class Names of Organic Compounds and Reactive Intermediates Based on Structure (IUPAC Recommendations 1995), Pure & Appl. Chem., 67(8/9):1307-1375 (1995).
https://www.britannica.com/science/oligosaccharide, Mar. 28, 2020.
https://www.ncbi.nlm.nih.gov/books/NBK453086/?report-=printable, Mar. 28, 2020.

* cited by examiner

R  =  Na⁺; Ka⁺; Ca²⁺; Mg²⁺; NH₄⁺; Li⁺;
X  =  OH⁻; CO₃²⁻; HCO₃⁻; CH₃O⁻; CH₃CH₂O⁻; (CH₃)₃CO⁻

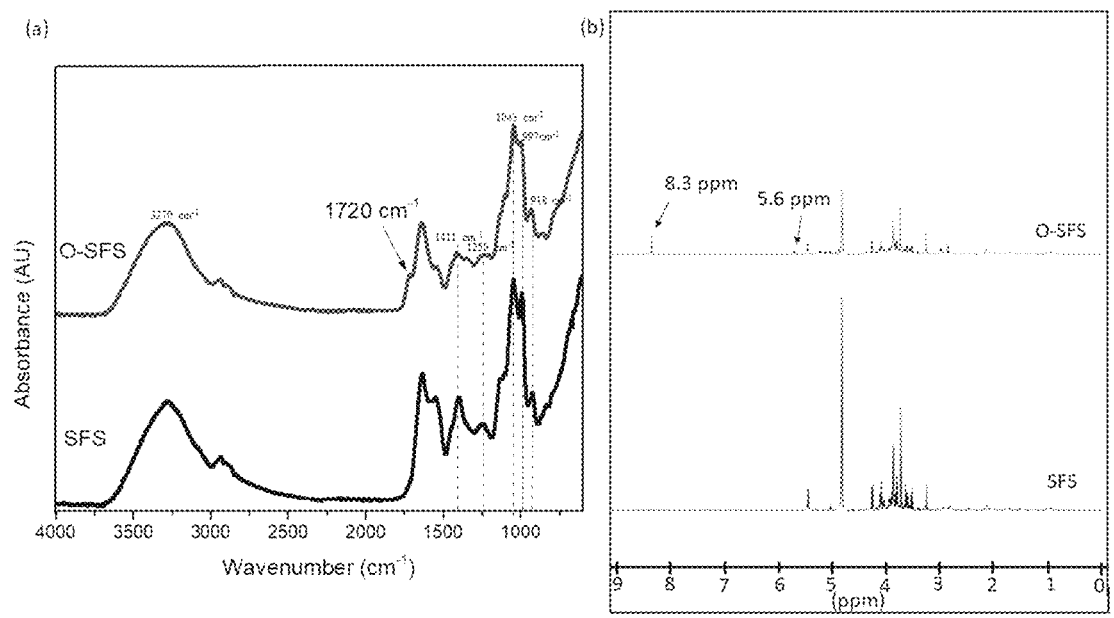
Figure 24A      Figure 24B
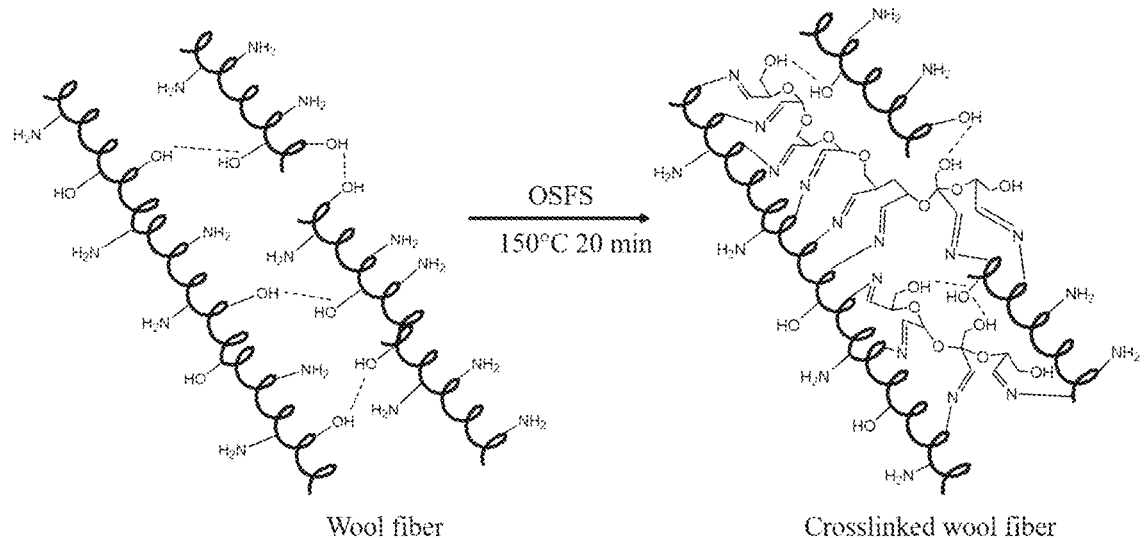
Figure 25

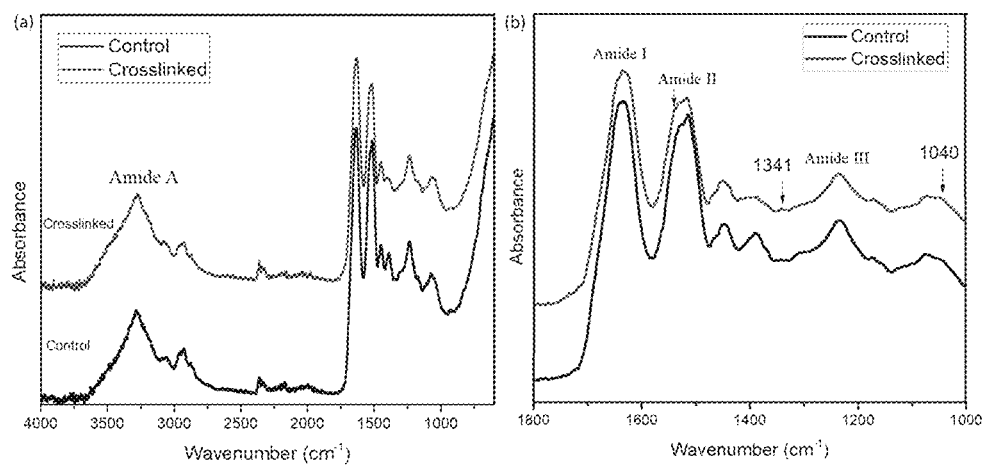
Figure 26A    Figure 26B
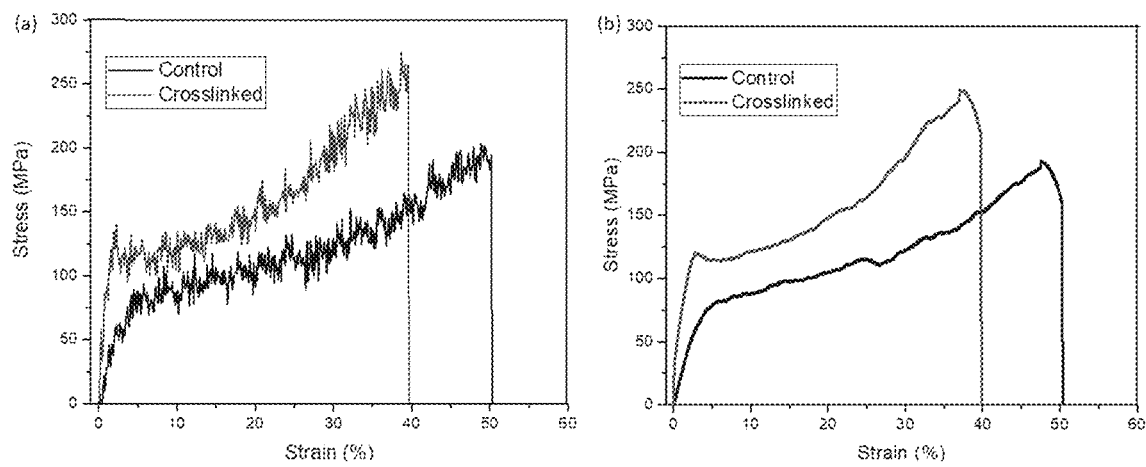
Figure 27A    Figure 27B

RESIDUAL SOY FLOUR SUGARS AS CROSSLINKERS FOR ENHANCING MECHANICAL PERFORMANCE OF PROTEIN FIBERS

CROSS-REFERENCE TO RELATED APPLICATIONS

This application claims priority benefit of U.S. Provisional Patent Application Ser. No. 62/815,279, filed Mar. 7, 2019, and is a continuation-in-part of U.S. patent application Ser. No. 15/307,828, filed Oct. 30, 2016, which is a U.S. National Phase filing under 35 U.S.C. § 371 of International Application No. PCT/US2015/028959, filed May 1, 2015, and published as WO 2015/168662 A1 on Nov. 5, 2015, which claims priority benefit of U.S. Provisional Patent Application Ser. No. 61/987,328, filed May 1, 2014, the disclosures of which are hereby incorporated by reference herein in their entirety.

FIELD OF THE INVENTION

The present disclosure relates to, inter alia, a green technology for crosslinking protein molecules for various uses, where the protein molecules can be contained in protein fibers such as, but not limited to, human hair, animal fibers, and mixtures thereof.

The present disclosure also relates to, inter alia, a green technology for enhancing strength of protein fibers, including without limitation wool fibers, using a soy flour sugar-based 'green' crosslinker.

BACKGROUND OF THE INVENTION

Treating human hair for cosmetic purposes and treating animal fibers to produce useful consumer products often involve harsh chemical-based and/or environmentally damaging processes. Regarding the treatment of human hair, changing the state of the hair from curly and kinky to straight or from straight to curly is one of the most common hair treatments for all human beings, particularly for the women. There are many ways to obtain the desired state of hair (e.g., straight, curly, kinky, etc.). For example, using a flat-iron for hair straightening and using rolls and curling irons for obtaining hair curls are two the most common methods practiced. However, both of these treatments are temporary and must use higher temperatures for obtaining the best results. Further, when the hair is washed, the straightness or curliness can be easily lost. Undesired loss of straightness or curliness may also occur when the hair is exposed to humid environment.

For a more permanent treatment of hair or animal fibers/fabrics, the use of chemicals, particularly harsh chemicals, is common. For example, in a typical process for a lasting treatment of hair, the hair is saturated with a solution containing a chemical compound that breaks the bonds that give each strand its shape. Thereafter, the hair is then rinsed, blow-dried, and meticulously flat-ironed to reach the desired shape. Once a 'neutralizer' is applied, the hair is locked into this new, straight configuration. The process can take up to eight hours the first time (depending on length and thickness), while touch-ups require three to four hours. Generally, for a short period after the treatment (e.g., three days), the treated hair should not be wetted or manipulated in such a way that would induce kink (e.g., like wearing a ponytail). While the hair will now be sleek and shiny (even after air-drying), bone-straight may be the only styling option. Even curling irons or hot rollers will not restore the volume or wave. Therefore, there is a need for more permanent solutions to hair treatment processes that are also not dependent on harsh chemical or high temperatures that could harm the hair.

With regard to producing fabrics based on animal fibers, there is a deficiency in the art of environmentally friendly methods in maintaining the fabrics in a particular form (e.g., pleated, wrinkle-free, creased, flattened).

Wool is the most important animal fiber used in textiles and many other applications. It is a fully renewable but expensive fiber that is known for its comfort, warmth retention, moisture absorption and elasticity. While wool is most commonly obtained from sheep, hair from other animals such as goats, llamas and alpacas are also used. The fleece (raw wool) obtained from the animals contains 30-70% impurities such as sand, dirt, grease, dried sweat, etc., most of which are removed through the scouring process. The cleaned dry wool is commonly processed through a carding machine and comber to produce a continuous web or sliver (wool top) with individual fibers parallel to each other. The length of fibers in the sliver can vary from 2 to 6 inches depending on the wool variety and the processes used. Sliver is drawn to desired linear density and twisted during spinning to form continuous yarn. Since wool fibers are inherently weak, fiber breakage during spinning and weaving processes, which are commonly carried out under tension, is a significant problem. Fiber breakages reduce the production efficiency, create fabric defects and generate significant amounts of fiber and fabric wastes. Increasing the strength of the fibers can not only solve these issues but also allow spinning finer yarns from the same fibers, significantly increasing its value.

There have been many improvements in the genetic modifications of wool by selective breeding of sheep as well as by providing better nutrition to increase the length, fineness, yield, and strength of the fiber. Some plasma treatment of wool fibers have also shown to reduce fiber breakage during the spinning process. Genetic modifications and plasma treatments, however, can be expensive. Chemical crosslinking can be much less expensive and an easier way to enhance the tensile properties of the fiber. The chemical composition of wool has shown presence of many polar and non-polar amino acids. Amino acids with polar groups, e.g., in soy proteins, have shown excellent possibilities for chemical modifications through crosslinking. While the exact content of polar amino acids varies based on the source, high contents of amino acids such as arginine (19.1%), serine (8.7%), glutamic acid (8.5%) and cystine (7.3%) have been found in merino wool. Amino acids with acidic side chains such as glutamic acid, aspartic acid, asparagine, glutamine account for about 10% of the total amino acids. Amino acids with basic side chains such as lysine, histidine, tryptophan account for 3.5%. Threonine and tyrosine are amino acids with hydroxyl groups in the side chain and account for 9% of the total amino acids. Glycine, leucine, proline, valine, alanine, isoleucine and phenylalanine, amino acids without reactive groups on their side chains account for about 30% of amino acids. In most crosslinking cases involving proteins, bifunctional crosslinkers such as glyoxal, glutaraldehyde, diisocyanates and carbodiimides have been used. Some formaldehyde-based crosslinkers have also been reported. These crosslinkers are skin irritant and toxic, not only to cells and biological systems but also to the environment. As a result, they pose a great danger to the health of the users. Formaldehyde has been classified as a carcinogen and is being banned in many places.

Soybean, a legume species, is an important agricultural and industrial crop. It is one of the major oilseeds produced in the US and worldwide. Soybean makes up over half of all the oilseeds in the world market. There has been an increase in the use of soybean oil to produce biodiesel in the last few years. Apart from oil, soybeans are also a major source of edible plant-based protein. Defatted soy flour (SF) is obtained as a by-product after extracting oil from soybeans. It consists of 50-54% protein, 30-32% carbohydrate, 2-3% dietary fibers and other minor components such as minerals, ash and moisture. SF is purified to obtain soy protein concentrate (SPC) and further purified to get soy protein isolate (SPI). The purification process involves removing the 30-32% carbohydrates present in SF. The carbohydrate mixture, a by-product of SPC and SPI production is generally discarded as waste. It consists of five different sugars: monosaccharides (fructose and glucose), disaccharide (sucrose), trisaccharide (raffinose) and tetrasaccharide (stachyose). Raffinose and stachyose are not digestible by humans or animals. These sugars, as a mixture, can be modified and utilized for non-edible purposes.

There is a need for new and improved technologies for enhancing strength of wool fiber.

The present invention is directed to overcoming these and other deficiencies in the art.

SUMMARY OF THE INVENTION

In various aspects, the present invention relates to, inter alia, green technology for crosslinking protein fibers, including, without limitation, fibers such as woolen, hair, and other protein fibers for various uses. In one embodiment, the present invention relates to a green technology for cross-linking of hair (including human hair or non-human hair), and other protein fibers, to obtain stiffness, long lasting straightness, curliness or frizz, or other desired three dimensional structures. In another embodiment, the present invention relates to a green technology for crosslinking of woolen and other protein fiber based fabrics to increase their crease retention and stiffness.

In one aspect, the present disclosure provides a method of crosslinking protein fibers. The method involves: (i) providing a crosslinking agent comprising an oxidized sugar having at least two aldehyde groups; and (ii) infiltrating a plurality of non-crosslinked protein fibers with the crosslinking agent under conditions effective to cause protein molecules contained in the non-crosslinked protein fibers to become crosslinked, thereby yielding a population of crosslinked protein fibers. The protein molecules of the non-crosslinked protein fibers comprise amine groups that react with the aldehyde groups of the oxidized sugar to achieve the crosslinking of the protein molecules to yield the crosslinked protein fibers.

In another aspect, the present disclosure provides a formulation for crosslinking protein fibers. The formulation includes a crosslinking agent comprising a plurality of oxidized sugars having at least two aldehyde groups, where the crosslinking agent is formulated so that the aldehyde groups of the oxidized sugars are effective to react with amine groups of protein molecules contained in the non-crosslinked protein fibers to yield a population of crosslinked protein fibers.

In a further aspect, the present disclosure provides a method of treating human hair to maintain a desired three dimensional structure. This method involves: (i) providing a formulation as described herein; and (ii) treating a population of human hair with the formulation so as to maintain the desired three dimensional (3D) structure of the population of human hair, where the human hair comprises non-cross-linked protein fibers having protein molecules having amine groups that react with the aldehyde groups of the oxidized sugar of the formulation.

In another aspect, the present disclosure provides a method of treating animal fibers to maintain a desired three dimensional structure. This method involves: (i) providing a formulation as described herein; and (ii) treating a population of animal fibers with the formulation so as maintain the desired three dimensional (3D) structure of the population of the animal fiber, where the animal fiber comprises non-crosslinked protein fibers having protein molecules having amine groups that react with the aldehyde groups of the oxidized sugar of the formulation.

In another aspect, the present disclosure provides a fabric comprising the treated animal fibers produced according to the corresponding method as described herein.

In a further aspect, the present disclosure provides a method of making a formulation for crosslinking protein fibers. This method involves: (i) providing a mixture of non-oxidized sugar molecules; and (ii) reacting the non-oxidized sugar molecules with a benign oxidizing agent to cause oxidation of the non-oxidized sugar molecules to yield a formulation comprising a mixture of oxidized sugar molecules having at least two aldehyde groups, where the mixture of oxidized sugar molecules are crosslinking agents effective to react with amine groups of protein molecules contained in non-crosslinked protein fibers to yield a population of crosslinked protein fibers.

In another aspect, the present disclosure provides a formulation produced according to the corresponding method as described herein.

In a further aspect, the present disclosure provides a method of preparing a crosslinking agent. This method involves: (i) providing a mixture of non-oxidized sugar molecules; and (ii) reacting the non-oxidized sugar molecules with a benign oxidizing agent to cause oxidation of the non-oxidized sugar molecules to yield a mixture of oxidized sugar molecules having at least two aldehyde groups, said oxidized sugar molecules corresponding a crosslinking agent effective to infiltrate non-crosslinked protein fibers to yield a population of crosslinked protein fibers.

In another aspect, the present disclosure provides a cross-linking agent produced according to the corresponding method as described herein.

In various other aspects, the present disclosure relates to, inter alia, residual sugars (e.g., soy flour sugars) and/or sugar mixtures as crosslinkers for enhancing mechanical performance of protein fibers, including, without limitation, fibers such as woolen, hair, and other protein fibers for various uses. Enhanced mechanical performance can include, without limitation, improved tensile properties (e.g., increased tensile strength, increased Young's modulus, etc.). Certain of these aspects are described below.

In one aspect, the present disclosure provides a method of crosslinking protein fibers. The method involves: (i) providing a crosslinking agent comprising an oxidized sugar mixture comprising a plurality of different oxidized sugars of different molecular lengths and having at least two aldehyde groups; and (ii) infiltrating a plurality of non-crosslinked protein fibers with the crosslinking agent under conditions effective to cause protein molecules contained in the non-crosslinked protein fibers to become crosslinked, thereby yielding a population of crosslinked protein fibers, wherein the protein molecules of the non-crosslinked protein fibers comprise amine groups that react with the aldehyde groups of the oxidized sugars to achieve the crosslinking of the protein molecules to yield the crosslinked protein fibers.

In another aspect, the present disclosure provides a method of making a crosslinking formulation for crosslinking protein fibers. This method involves: (i) providing a mixture of non-oxidized sugar molecules comprising a plurality of different sugars of different molecular lengths; and (ii) reacting the non-oxidized sugar molecules with an oxidizing agent comprising sodium periodate ($NaIO_4$) to cause oxidation of the non-oxidized sugar molecules to yield a crosslinking formulation comprising an oxidized sugar mixture comprising a plurality of different oxidized sugars of different molecular lengths and having at least two aldehyde groups, wherein said mixture of oxidized sugars are crosslinking agents effective to react with amine groups of protein molecules contained in non-crosslinked protein fibers to yield a population of crosslinked protein fibers.

In another aspect, the present disclosure provides a crosslinking formulation produced according to the above method.

In another aspect, the present disclosure provides a method of treating animal fibers to improve their tensile properties. This method involves: (i) providing a crosslinking formulation according to the present disclosure; and (ii) treating a population of non-crosslinked animal fibers with the crosslinking formulation so as to yield a population of crosslinked animal fibers having improved tensile properties as compared to the population of non-crosslinked animal fibers, wherein the population of non-crosslinked animal fibers comprises non-crosslinked animal protein fibers having protein molecules having amine groups that react with the aldehyde groups of the different oxidized sugars of the crosslinking formulation.

In another aspect, the present disclosure provides a fabric comprising the treated animal fibers produced according to the above method.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

(iii) unfolded and dried in oven (80° C.); and (iv) steam ironed flat (2 min per side). The fabric retained creases even after washing in water, drying in an oven and ironing flat.

Figure 20:
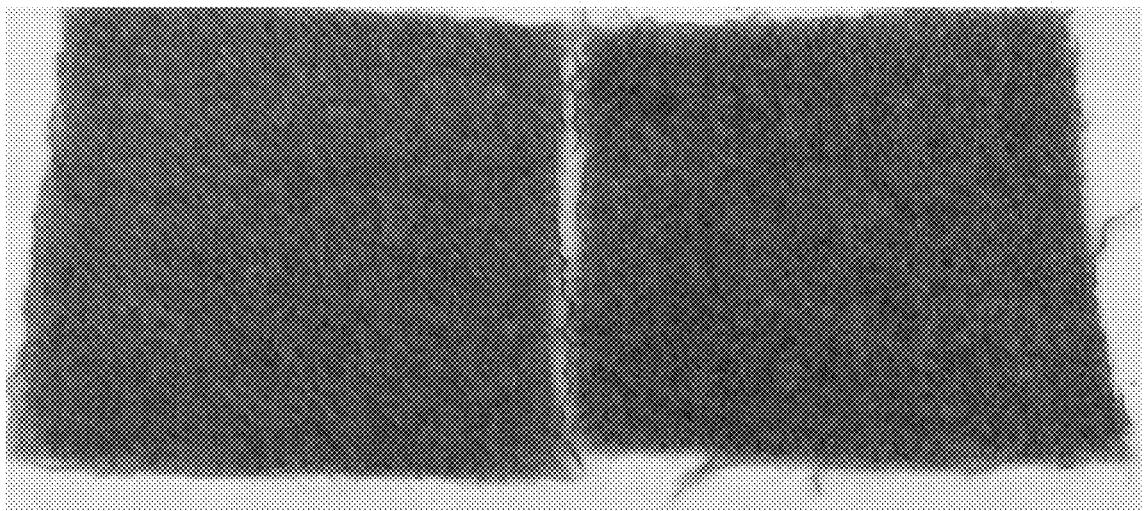

FIG. 20 is a photograph of a woolen fabric treated with oxidized sucrose solution. The fabric was ironed flat (ironed 5 min per side). This illustrates that the treated fabric can be ironed flat (initially).

Figure 21A:
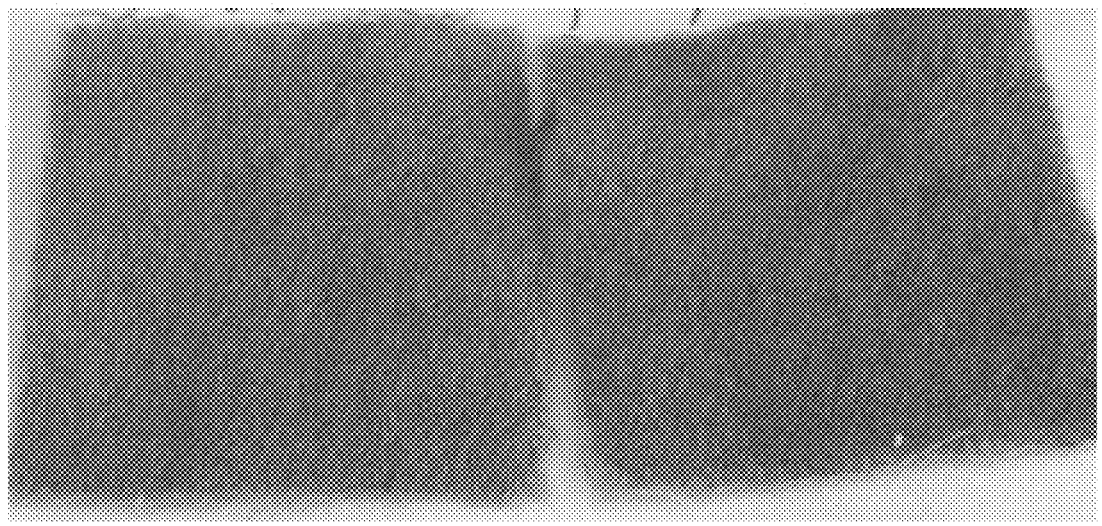
Figure 21B:
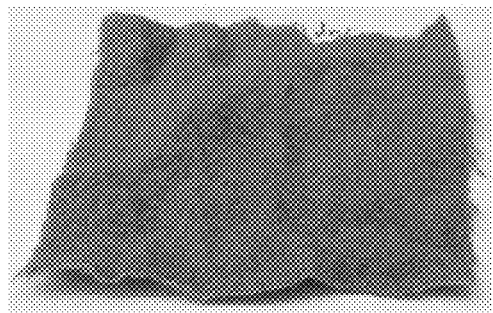

FIGS. 21A-21B are photographs of woolen fabric treated with oxidized sucrose solution and non-treated woolen fabric. The fabric was (i) ironed flat; (ii) washed with detergent (300 mL 0.36% Tide for 15 min, rinsed with large amount of water); and (iii) dried in oven (80° C.). FIG. 21A shows the treated fabric having no wrinkles (right side) as compared to untreated fabric sample (left side). FIG. 21B shows an untreated control woolen fabric showing wrinkles.

Figure 22:
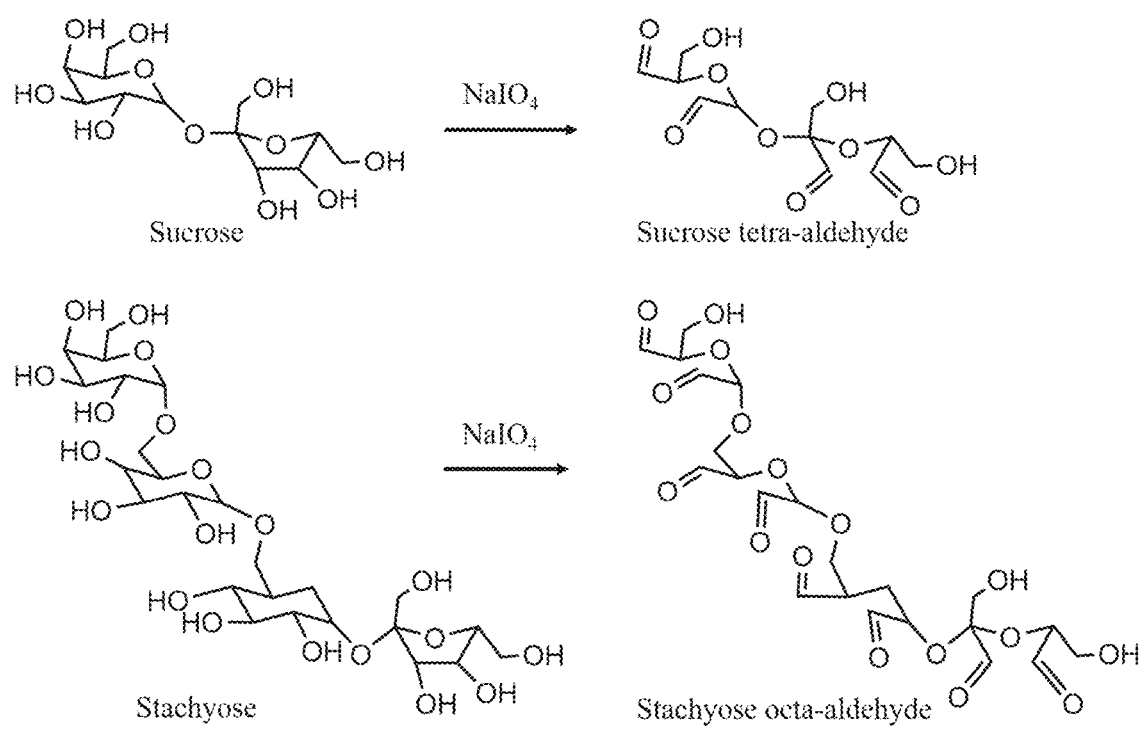

FIG. 22 is a schematic of proposed reactions for oxidation of sucrose and stachyose in accordance with embodiments of the present disclosure.

Figure 23:
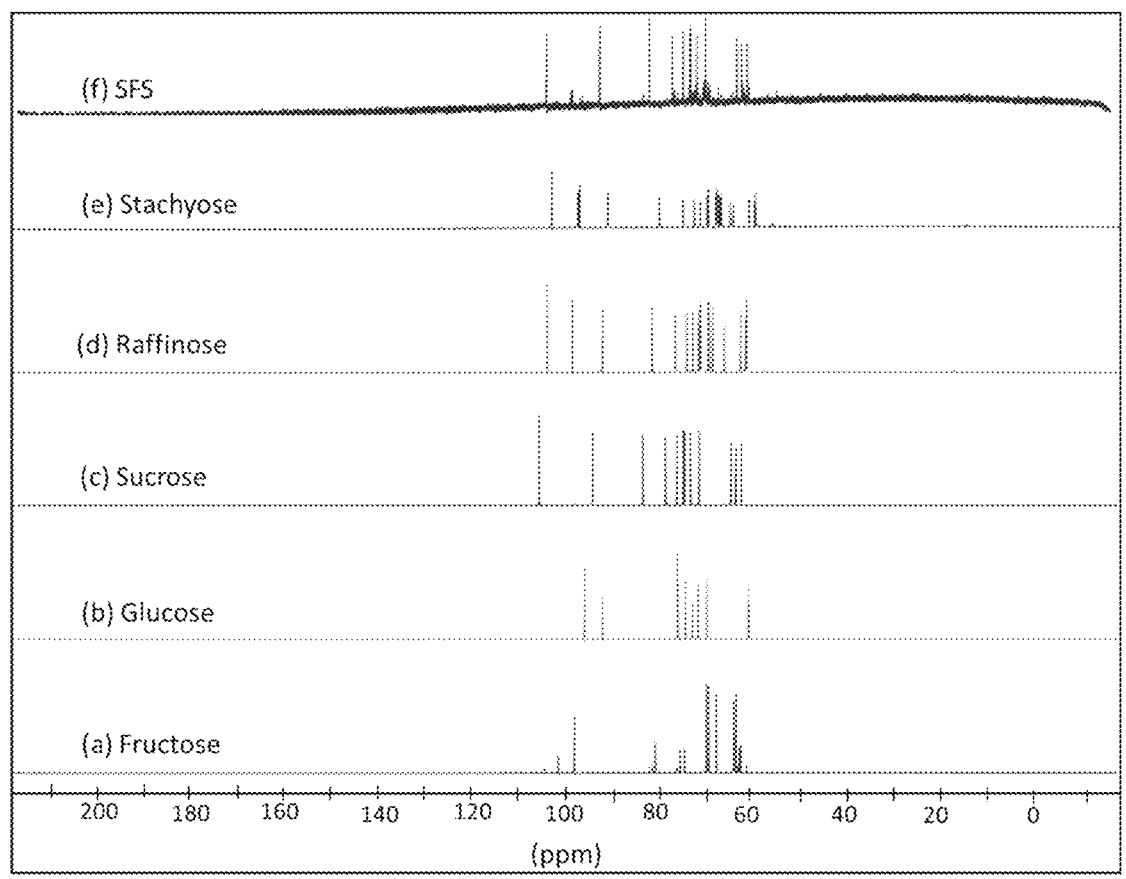

FIG. 23 is as graph illustrating $^{13}C$ NMR spectra of (a) Fructose, (b) Glucose, (c) Sucrose, (d) Raffinose, (e) Stachyose, and (f) SFS.

FIGS. 24A-24B are ATR-FTIR spectra (FIG. 24A) and $^1$HNMR spectra (FIG. 24B) of SFS and OSFS.

FIG. 25 is a schematic illustrating crosslinking of wool fibers using OSFS by Schiff's base (imine) formation.

FIGS. 26A-26B are ATR-FTIR spectra of control and crosslinked wool fibers from 4000 $cm^{-1}$ to 500 $cm^{-1}$ (FIG. 26A) and 1800 $cm^{-1}$ to 1000 $cm^{-1}$ (FIG. 26B).

FIGS. 27A-27B are typical stress-strain plots for control and crosslinked fibers. FIG. 27A: original. FIG. 27B: smoothened.

FIGS. 28A-28D are SEM images of surface of control (FIGS. 28A and 28B) and crosslinked (FIGS. 28C and 28D) wool fibers.

FIGS. 29A-29D are SEM images of fractured ends of control (FIGS. 29A and 29B) and crosslinked (FIGS. 29C and 29D) wool fibers.

Figures 30A, 30B, 30C, 30D, 30E, 30F:
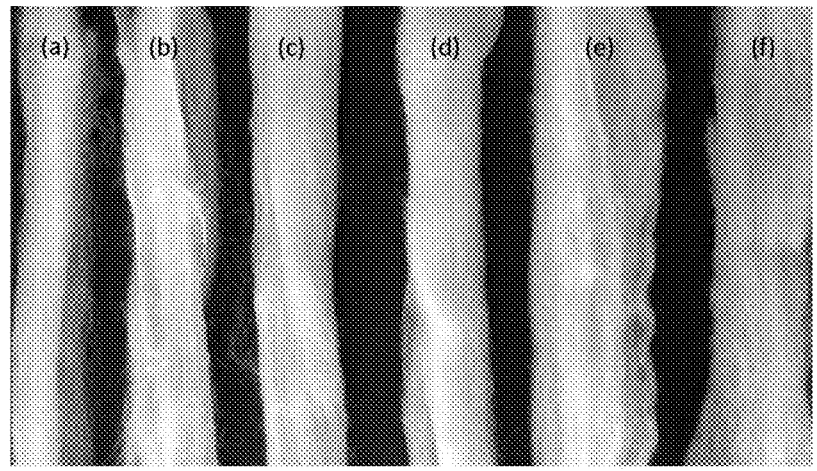

FIGS. 30A-30F are pictures of control and treated wool slivers: FIG. 30A: control, FIG. 30B: wool-SFS, FIG. 30C: wool-OSFS MR 1, FIG. 30D: wool-OSFS MR 1.5, FIG. 30E: wool-OSFS MR 2, and FIG. 30F: wool-OSFS MR 2.5. All treatments carried out at 150° C. for 20 min.

Figure 31:
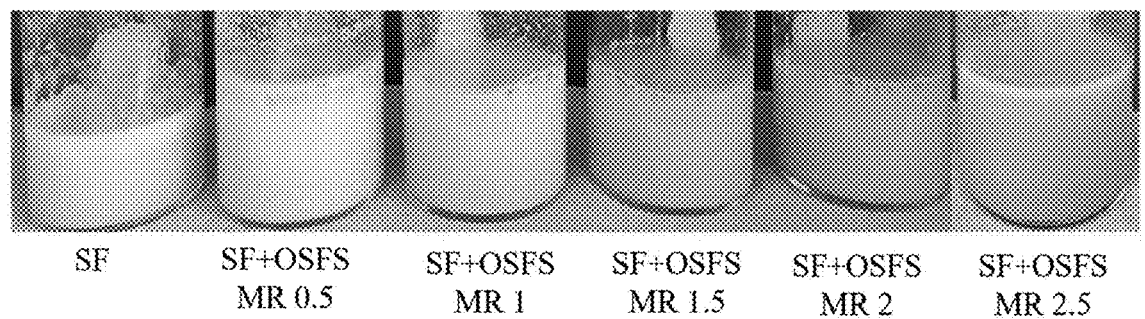

FIG. 31 are photographs illustrating the effect of addition of OSFS with different molar ratios of $NaIO_4$:SFS from 0.5 to 2.5 on the color of SF.

Figures 32A, 32B, 32C:
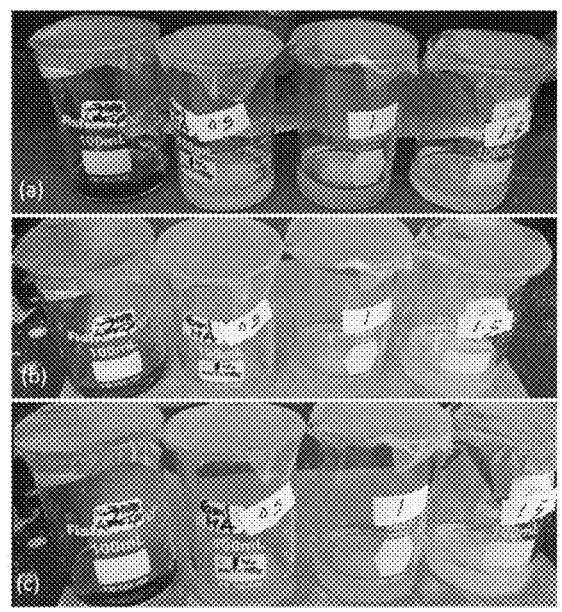

FIGS. 32A-32C are photographs illustrating $BaCl_2$:$NaIO_4$ molar ratios of 0, 0.5, 1 and 1.5 (across a, b and c) added to OSFS 15 min refrigerated (FIG. 32A), 30 min refrigerated (FIG. 32B), and 1 h refrigerated (FIG. 32C).

DETAILED DESCRIPTION OF THE INVENTION

The present disclosure relates to, inter alia, a green technology for crosslinking protein molecules for various uses, where the protein molecules can be contained in protein fibers such as, but not limited to, human hair, animal fibers, and mixtures thereof. The green technology of the present disclosure provides crosslinking agents, formulations, and methods of making and using such crosslinking agents and formulations. In regard to one particular advantage of the green technology of the present disclosure over the existing art of treating hair or animal fibers, the presently disclosed green technology does not require the use of harsh chemicals or harmfully high temperatures to achieve permanent or substantially improved permanence of the desired structural changes from the hair or animal fiber treatments.

Provided below is a more detailed description of the various aspects of the green technology of the present disclosure.

As used herein, the term "protein fibers" refers to any fiber material that includes protein as a component of the fiber. Protein fibers of the present disclosure include, without limitation, any fibers that contain protein molecules, and particularly protein molecules that have amino acids with functional groups (e.g., amine groups) that can react with an aldehyde group (e.g., to form a bond or link). Non-limiting examples of amino acids with such suitable functional groups include amino acids such as arginine and lysine. Non-limiting examples of particular types of protein fibers of the present disclosure are keratin-containing fibers.

As provided herein, "keratin-containing fibers" can include, without limitation, human hair, animal fibers, or a mixture thereof. In accordance with the present disclosure, the human hair can be any type of hair, regardless of the color, three dimensional structure, age, texture, fineness, etc. In accordance with the present disclosure, the animal fibers can include, without limitation, wool, alpaca, angora, fur, cashmere, mohair, qiviut, or mixtures and variations thereof. Non-limiting examples of animals that can provide the animal fibers of the present disclosure include animals such as sheep, vicuna, alpaca, llama, muskox, goats, bison, camel, yak, horse, chinchilla, rabbit, or related species thereof. Further, as in accordance with the present disclosure, the animal fibers can have various forms, including, without limitation, forms such as raw fibers, yarns, felts, woven or knitted fabrics, and the like.

As used herein to describe human hair or animal fibers or animal fabrics, the term "three dimensional structure" (3D structure) refers to the structural shape of the hair, animal fiber, or animal fabric. Non-limiting examples of 3D structures of human hair can include straight hair, wavy hair, curly hair, kinky hair, or variations thereof. Non-limiting examples of 3D structures of animal fibers or animal fabrics can include forms such as creased fabrics, non-creased fabrics, pleated fabrics, flat fabrics, roughened surface fabrics, wrinkled fabrics, and variations thereof.

As described herein, the green technology of the present disclosure involves the use of a crosslinking agent. As used herein, the term "crosslinking agent" refers to an agent that includes an oxidized sugar, and particularly an oxidized sugar that includes at least two aldehyde groups. The sugar of the oxidized sugar can include or be based on monosaccharides, disaccharides, trisaccharides, tetrasaccharides, and oligosaccharides. Non-limiting examples of particular types of sugars in accordance with the present disclosure include galactose, sucrose, maltose, lactose, raffinose, stachyose, and mixtures thereof.

Figure 1:
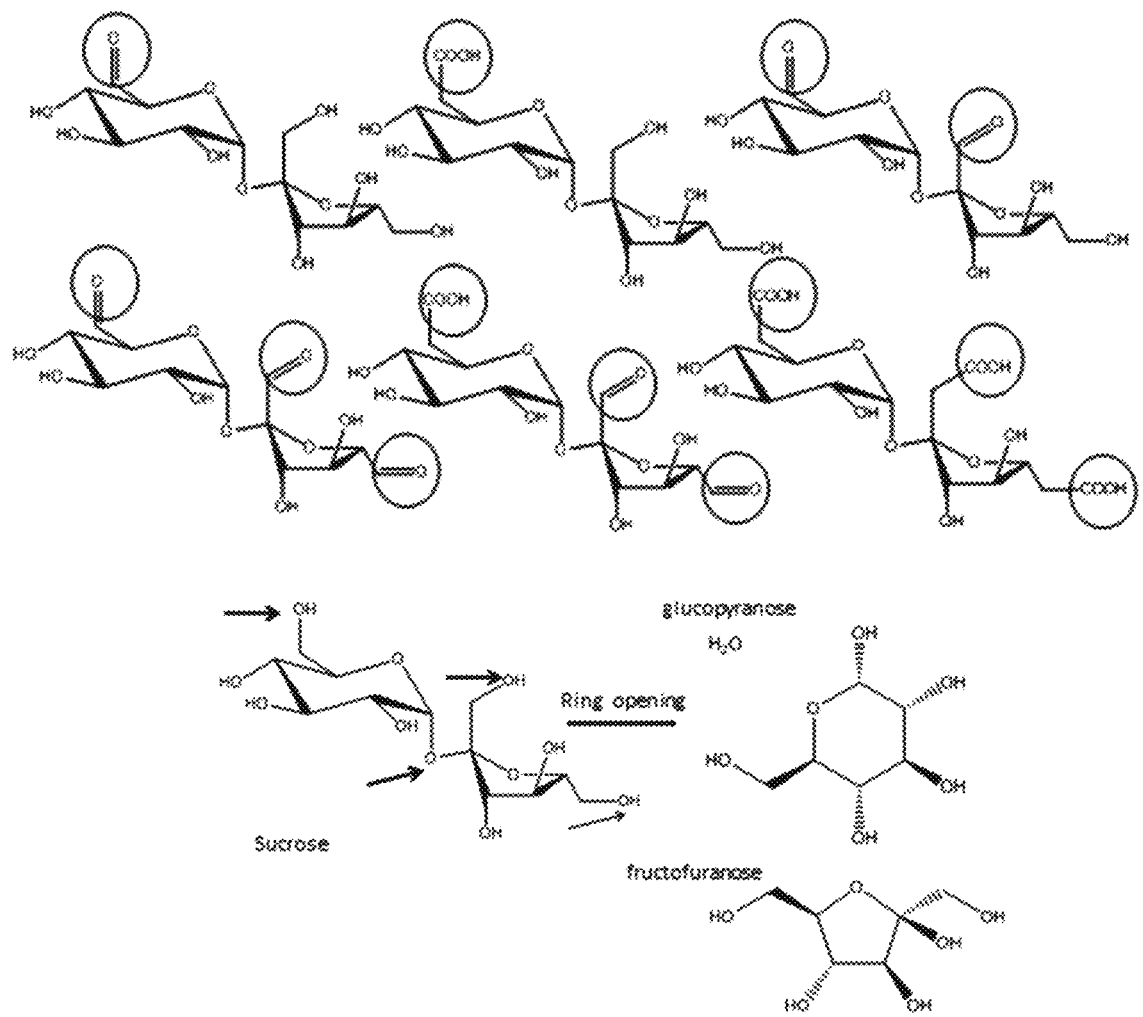
FIG. 1 is a scheme of an oxidation process of sucrose.
Figure 2:
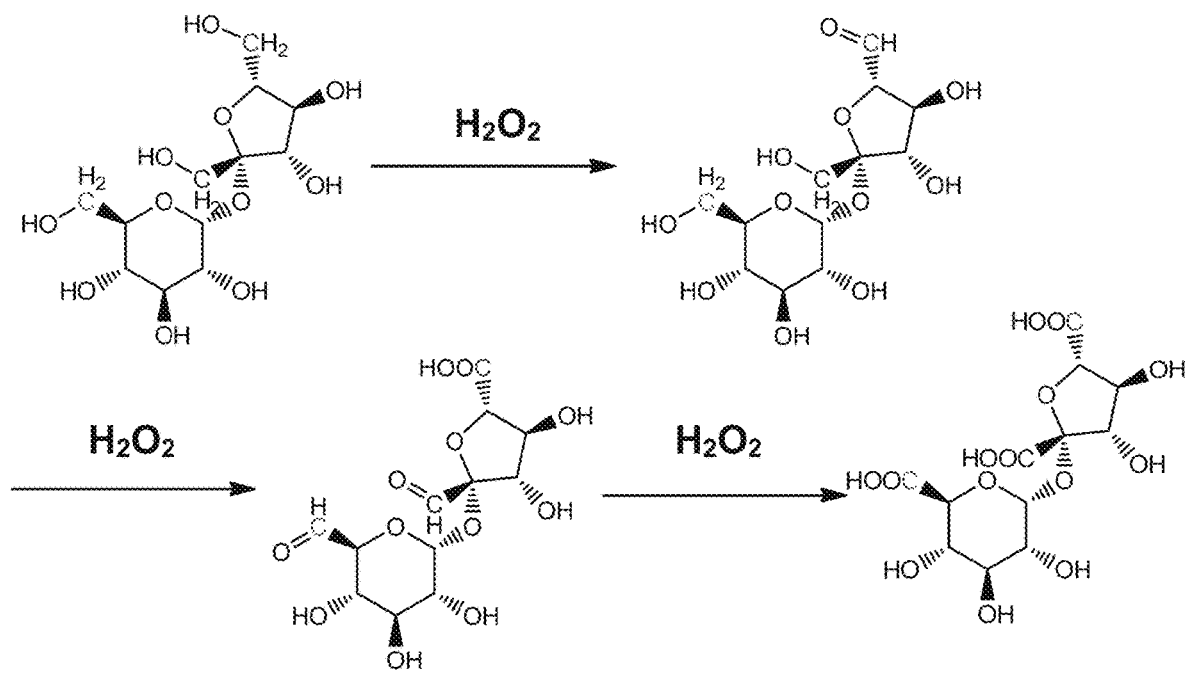
FIG. 2 is a scheme illustrating the oxidation of sucrose using hydrogen peroxide ($H_2O_2$) as the benign oxidizing agent, with aldehyde groups and subsequent carboxyl groups being formed during the oxidation process.
Figure 3:
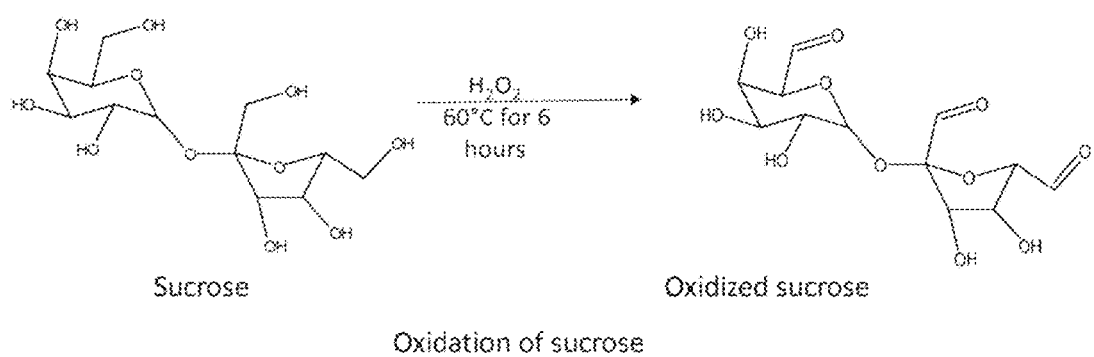
FIG. 3 is a scheme illustrating the oxidation of sucrose using hydrogen peroxide ($H_2O_2$) as the benign oxidizing agent.
Figure 4:
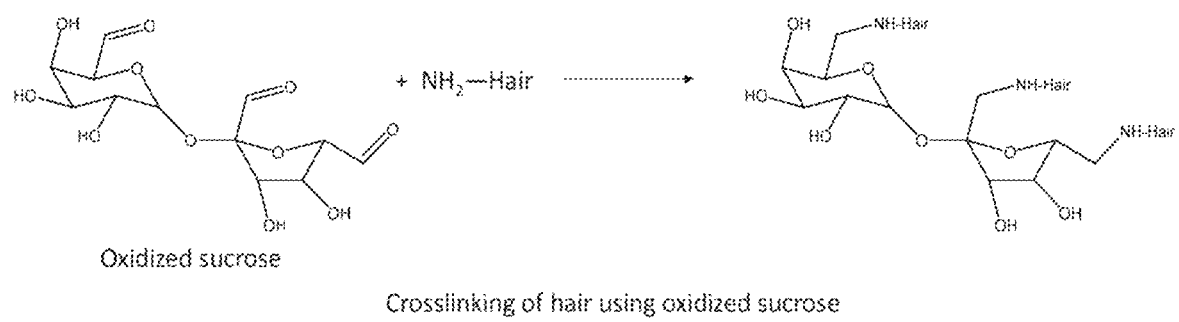
FIG. 4 is a scheme illustrating crosslinking of hair using oxidized sucrose.
Figure 5:
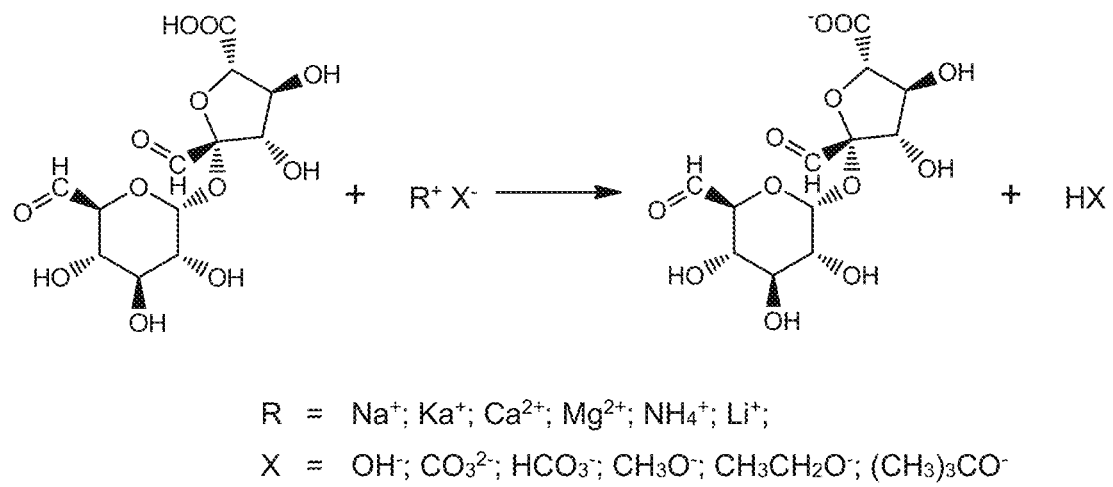
FIG. 5 is a scheme illustrating the chemistry of neutralization of oxidized sucrose, where hydrogen peroxide ($H_2O_2$) is used as the benign oxidizing agent.

FIG. 1 illustrates one scheme for the oxidation of sugar to yield oxidized sugar products that can be used as crosslinking agents of the present disclosure. The scheme of FIG. 1 shows the oxidation of sucrose, which scheme is further described in Dastidar et al., *Green Chemistry*, 15:3243-3251 (2013), which is hereby incorporated by reference herein in its entirety. FIG. 2 and FIG. 3 are also schemes for the oxidation of sugars, particularly sucrose, where hydrogen peroxide ($H_2O_2$) is used as the benign oxidizing agent. FIG. 4 illustrates a scheme of the crosslinking of hair using oxidized sugar produced by the scheme of FIG. 3. FIG. 5 is a scheme showing the chemistry of neutralization of oxidized sucrose, where hydrogen peroxide ($H_2O_2$) is used as the benign oxidizing agent.

In one aspect, the present disclosure provides a method of crosslinking protein fibers. The method involves: (i) providing a crosslinking agent comprising an oxidized sugar having at least two aldehyde groups; and (ii) infiltrating a plurality of non-crosslinked protein fibers with the crosslinking agent under conditions effective to cause protein molecules contained in the non-crosslinked protein fibers to become crosslinked, thereby yielding a population of crosslinked protein fibers. The protein molecules of the non-crosslinked protein fibers comprise amine groups that react with the aldehyde groups of the oxidized sugar to achieve the crosslinking of the protein molecules to yield the crosslinked protein fibers.

As used herein, the term "infiltrating" generally refers to a process by which a crosslinking agent infiltrates protein fibers so as to allow the crosslinking agent to react with the protein molecules contained in the protein fibers. Once the crosslinking agent reacts with the protein molecules, the protein molecules can then be crosslinked, thereby resulting in protein fibers that are then considered crosslinked. The term "diffusion" can also be used to describe this infiltrating or infiltration of the crosslinking agent into the protein fibers.

In one embodiment, the crosslinking agent is an aqueous solution having at least 1-60 weight percent of the oxidized sugar.

In a particular embodiment of this method, the infiltrating step is carried out at a temperature selected from the group consisting of less than 100° C., less than 90° C., less than 80° C., less than 70° C., less than 60° C., less than 50° C., less than 40° C., less than 30° C., and less than 20° C., and for a length of time sufficient to yield the population of crosslinked protein fibers at said temperature used for carrying out the infiltrating step. Generally, the lower the temperature, the longer the time is needed for infiltration or diffusion to occur. Non-limiting examples of suitable infiltration times can range from seconds to hours, including, for example, a range of less than a minute to less than 10 minutes, as well as a range of about 10 minutes to 4 hours or more, depending on the temperature used.

In accordance with the present disclosure, in certain embodiments of this method, the infiltrating step is carried out at a pH of between about 7 and about 12, or more particularly at a pH of between about 10 and about 12. Generally, a higher pH is preferred as it relaxes hair and wool and increases infiltration/diffusion of the crosslinking agent of the present disclosure (i.e., the oxidized sugar).

In another embodiment, this method can further comprise heating the population of crosslinked protein fibers at a temperature of between about 100° C. and about 220° C. for a period of time of between about 3 seconds and about 120 seconds to substantially complete the crosslinking. In a particular embodiment, the temperature of the heating step can range from about 120° C. to about 220° C., and more particularly from about 140° C. to about 160° C. Temperatures below 220° C. and even below 160° C. are preferred in certain embodiments where there is a concern about extensive damage to the protein fibers, particularly to human hair. In accordance with the present disclosure, protein fibers such as animal fibers (like wool) can withstand temperatures at the higher end of the range of temperatures.

In a particular embodiment of this method, the heating step is carried out by applying a source of heat to the population of crosslinked protein fibers. As used herein, the concept of "heating" the protein fibers is meant to refer to the process of subjecting the protein fibers to a particular raised temperature. Therefore, when describing the temperature of the heating step, reference is made to the "ambient temperature" and not the temperature of the protein fibers themselves (e.g., human hair or animal fibers).

Non-limiting examples of the source of heat is for the heating step include sources such as a flat iron, hot rollers, a hot plate, a curling iron, a hair dryer, an iron, a clothes dryer, an oven, etc.

In another embodiment, this method further comprises washing the population of crosslinked protein fibers to remove residual crosslinking agent or to remove crosslinking agent adhering to the protein fibers, thereby substantially removing the crosslinking agent. In one particular embodiment, the washing is carried out using water or soap water. The soap water can include, without limitation, detergents, shampoo, and any other solution containing an agent effective to remove the residual crosslinking agent from the protein fiber mixture or to remove crosslinking agent adhering to the protein fibers.

In accordance with one embodiment of this method, the crosslinking agent is prepared according to a method comprising the steps of: (i) providing a mixture of non-oxidized sugar molecules; and (ii) reacting the non-oxidized sugar molecules with a benign oxidizing agent to cause oxidation of the non-oxidized sugar molecules to yield a reaction mixture comprising oxidized sugar molecules having at least two aldehyde groups, said oxidized sugar molecules corresponding to the crosslinking agent.

In one embodiment, the oxidation is carried out at a temperature selected from the group consisting of less than 100° C., less than 90° C., less than 80° C., less than 70° C., less than 60° C., less than 50° C., less than 40° C., and less than 30° C.

In one embodiment, the oxidation is carried out at a pH of between about 2 and about 4.

A suitable benign oxidizing agent can include any agent effective to oxidize sugar so that the oxidized sugar includes at least two aldehyde groups, where the agent is considered "green" as opposed to being more of a harsh or toxic chemical agent. A non-limiting example of a benign oxidizing agent is hydrogen peroxide ($H_2O_2$). In certain embodiments, the hydrogen peroxide ($H_2O_2$) is acidified.

In accordance with one embodiment, in preparing the crosslinking agent, the method further comprises introducing an enzyme to the reaction mixture to inhibit further oxidation of aldehyde groups of the oxidized sugar molecules to carboxyl groups. Suitable enzymes can include any enzyme that is effective to inhibit the oxidation of the sugar molecules. In particular embodiments, if the benign oxidizing agent is hydrogen peroxide ($H_2O_2$), the enzyme can be any enzyme effective to catalyze decomposition of the hydrogen peroxide into oxygen (O) and water ($H_2O$). Non-limiting examples of suitable enzymes for this purpose include any catalase (e.g., GC 118 enzyme by DUPONT®) and any peroxidase.

In accordance with one embodiment, the enzyme is introduced at a point in the oxidation reaction so as to yield a mixture of oxidized sugar molecules having a greater concentration of aldehyde groups as compared to carboxyl group.

In a further embodiment, this method further comprises removing residual amounts of the benign oxidizing agent after introducing the enzyme.

As described further herein, the method of crosslinking protein fibers of the present disclosure can involve maintaining as well as changing the three dimensional structure of a population of crosslinked protein fibers. In one embodiment of this method, the population of crosslinked protein fibers has an initial three dimensional (3D) structure. In a further embodiment of this method, the population of crosslinked protein fibers is further treated to form the population of crosslinked protein fibers into a second 3D structure that is different from its initial 3D structure. As provided in certain embodiments, the initial 3D structure and the second 3D structure are selected from the group consisting of a creased fabric, a non-creased fabric, a pleated fabric, wrinkled, wrinkle-free, straight hair, wavy hair, curly hair, kinky hair, and variations thereof, as well as any other 3D structures described elsewhere herein or known in the art.

In another aspect, the present disclosure provides a formulation for crosslinking protein fibers. The formulation includes a crosslinking agent comprising a plurality of oxidized sugars having at least two aldehyde groups, where the crosslinking agent is formulated so that the aldehyde groups of the oxidized sugars are effective to react with amine groups of protein molecules contained in the non-crosslinked protein fibers to yield a population of crosslinked protein fibers.

In one embodiment, the formulation is in a form of a paste. In another embodiment, the formulation is in a form of an aqueous solution. In a particular embodiment, the aqueous solution comprises at least 40 weight percent of water. In another embodiment, the aqueous solution comprises at least 1-60 weight percent of the oxidized sugar. In a further embodiment, the formulation has a stable concentration of aldehyde groups. In a particular embodiment, the stable concentration of aldehyde groups is between about 20 and about 32 percent.

In accordance with the present disclosure, in certain embodiments, the formulation is substantially free of an oxidizing agent so that the stable concentration of aldehyde groups is maintained prior to reaction of the aldehyde groups with the amine groups of the protein molecules contained in the non-crosslinked protein fibers.

In a further aspect, the present disclosure provides a method of treating human hair to maintain a desired three dimensional structure. This method involves: (i) providing a formulation as described herein; and (ii) treating a population of human hair with the formulation so as to maintain the desired three dimensional (3D) structure of the population of human hair, where the human hair comprises non-crosslinked protein fibers having protein molecules having amine groups that react with the aldehyde groups of the oxidized sugar of the formulation.

As discussed herein, in certain embodiments of this method of treating human hair, the desired 3D structure of the human hair is selected from the group consisting of straight hair, wavy hair, curly hair, kinky hair, or variations thereof.

In one embodiment of this method, the treating step comprises infiltrating the non-crosslinked protein fibers with the crosslinking agent of the formulation to yield a population of crosslinked protein fibers having the desired 3D structure.

In accordance with one embodiment, the infiltrating step is carried out at a temperature selected from the group consisting of less than 100° C., less than 90° C., less than 80° C., less than 70° C., less than 60° C., less than 50° C., less than 40° C., less than 30° C., and less than 20° C., and for a length of time sufficient to yield the population of crosslinked protein fibers at said temperature used for carrying out the infiltrating step. For instance, as a non-limiting example, this step can be done when starting with curly hair, where curly hair is also the desired 3D structure.

In one embodiment of this method, the treating step comprises infiltrating the non-crosslinked protein fibers with the crosslinking agent of the formulation to yield an initial population of crosslinked protein fibers having an initial 3D structure that is not the desired 3D structure to be maintained.

In a further embodiment of this method, the method can also include manipulating the initial population of crosslinked protein fibers having the initial 3D structure so as to form into a final population of crosslinked protein fibers having the desired 3D structure.

In one embodiment, the manipulating step comprises heating the initial population of crosslinked protein fibers at a temperature of between about 100° C. and about 220° C. for a period of time of between about 3 seconds and about 120 seconds to substantially complete the crosslinking, where said heating is performed before, during, or after the forming of the initial population of crosslinked protein fibers into the final population of crosslinked protein fibers having the desired 3D structure.

In accordance with one embodiment, the heating is carried out by applying a source of heat to the population of crosslinked protein fibers. The source of heat can be, without limitation, selected from the group consisting of a flat iron, hot rollers, a hot plate, a curling iron, a hair dryer, an iron, a clothes dryer, an oven, etc.

In accordance with one embodiment of this method, the method can further comprise washing the population of crosslinked protein fibers to remove residual crosslinking agent or to remove crosslinking agent adhering to the protein fibers, thereby substantially removing the crosslinking agent. This method also can be such that the washing is carried out using water or soap water. The infiltrating step can be carried out at a pH of between about 7 and about 12.

In another aspect, the present disclosure provides a method of treating animal fibers to maintain a desired three dimensional structure. This method involves: (i) providing a formulation as described herein; and (ii) treating a population of animal fibers with the formulation so as maintain the desired three dimensional (3D) structure of the population of the animal fiber, where the animal fiber comprises non-crosslinked protein fibers having protein molecules having amine groups that react with the aldehyde groups of the oxidized sugar of the formulation.

In one embodiment, the desired 3D structure of the animal fiber is in a form of a fabric selected from the group consisting of a creased fabric, a non-creased fabric, a pleated fabric, a flat fabric, a roughened surface fabric, and variations thereof.

In accordance with one embodiment, treating step comprises infiltrating the non-crosslinked protein fibers with the crosslinking agent of the formulation to yield a population of crosslinked protein fibers having the desired 3D structure.

In accordance with one embodiment, the infiltrating step is carried out at a temperature selected from the group consisting of less than 200° C., less than 150° C., less than 100° C., less than 90° C., less than 80° C., less than 70° C., less than 60° C., less than 50° C., less than 40° C., less than 30° C., and less than 20° C., and for a length of time sufficient to yield the population of crosslinked protein fibers at said temperature used for carrying out the infiltrating step.

In accordance with one embodiment, treating step comprises infiltrating the non-crosslinked protein fibers with the crosslinking agent of the formulation to yield an initial population of crosslinked protein fibers having an initial 3D structure that is not the desired 3D structure to be maintained.

In one embodiment, the method further comprises manipulating the initial population of crosslinked protein fibers having the initial 3D structure so as to form into a final population of crosslinked protein fibers having the desired 3D structure.

In accordance with one embodiment, the manipulating step comprises heating the initial population of crosslinked protein fibers at a temperature of between about 100° C. and about 220° C. for a period of time of between about 3 seconds and about 120 seconds to substantially complete the crosslinking, where said heating is performed before, during, or after the forming the initial population of crosslinked protein fibers into the final population of crosslinked protein fibers having the desired 3D structure.

In accordance with one embodiment, the heating is carried out by applying a source of heat to the population of crosslinked protein fibers. In one embodiment, the source of heat is selected from the group consisting of a flat iron, an iron, a clothes dryer, an oven, etc.

In accordance with one embodiment, the method further comprises washing the population of crosslinked protein fibers to remove residual crosslinking agent or to remove crosslinking agent adhering to the protein fibers, thereby substantially removing the crosslinking agent. In one embodiment, the washing is carried out using water or soap water. In one embodiment, the infiltrating step is carried out at a pH of between about 7 and about 12.

In accordance with one embodiment, the animal fibers are selected from the group consisting of wool, alpaca, angora, fur, cashmere, mohair, and qiviut. In accordance with one embodiment, the animal fibers are from animals selected from the group consisting of sheep, vicuna, alpaca, llama, muskox, goats, bison, camel, yak, horse, chinchilla, and rabbit. In accordance with one embodiment, the animal fibers have a form selected from the group consisting of raw fibers, yarns, felts, and woven or knitted fabrics.

In accordance with one embodiment of this method, the sugar is selected from the group consisting of galactose, sucrose, maltose, lactose, raffinose, and stachyose.

In another aspect, the present disclosure provides a fabric comprising the treated animal fibers produced according to the corresponding method as described herein.

In a further aspect, the present disclosure provides a method of making a formulation for crosslinking protein fibers. This method involves: (i) providing a mixture of non-oxidized sugar molecules; and (ii) reacting the non-oxidized sugar molecules with a benign oxidizing agent to cause oxidation of the non-oxidized sugar molecules to yield a formulation comprising a mixture of oxidized sugar molecules having at least two aldehyde groups, where the mixture of oxidized sugar molecules are crosslinking agents effective to react with amine groups of protein molecules contained in non-crosslinked protein fibers to yield a population of crosslinked protein fibers.

In accordance with one embodiment of this method of making the formulation for crosslinking protein fibers, the method further comprises adding one or more of a preservative, a stabilizer, a filler, a coloring agent, a scent agent, a cosmetically acceptable carrier, an emulsifier, or mixtures thereof to the oxidized sugar molecules. The present disclosure contemplates the use of all such agents or compounds recognized by those of ordinary skill in the art.

In accordance with one embodiment, this method further comprises packaging the crosslinking agent under cosmetically suitable conditions to provide cosmetically acceptable shelf-life. Suitable packaging materials, designs, and packaging methods include any such materials, designs, or methods suitable for use in the relevant art.

In another aspect, the present disclosure provides a formulation produced according to the corresponding method as described herein.

In a further aspect, the present disclosure provides a method of preparing a crosslinking agent. This method involves: (i) providing a mixture of non-oxidized sugar molecules; and (ii) reacting the non-oxidized sugar molecules with a benign oxidizing agent to cause oxidation of the non-oxidized sugar molecules to yield a mixture of oxidized sugar molecules having at least two aldehyde groups, said oxidized sugar molecules corresponding a crosslinking agent effective to infiltrate non-crosslinked protein fibers to yield a population of crosslinked protein fibers.

In accordance with one embodiment of this method of preparing the crosslinking agent for crosslinking protein fibers, the method further comprises adding one or more of a preservative, a stabilizer, a filler, a coloring agent, a scent agent, a cosmetically acceptable carrier, an emulsifier, or mixtures thereof to the oxidized sugar molecules. The present disclosure contemplates the use of all such agents or compounds recognized by those of ordinary skill in the art.

In accordance with one embodiment, this method further comprises packaging the crosslinking agent under cosmetically suitable conditions to provide cosmetically acceptable shelf-life. Suitable packaging materials, designs, and packaging methods include any such materials, designs, or methods suitable for use in the relevant art.

As described herein, in certain aspects, the present disclosure provides a 'green' technology (e.g., methods, crosslinking agents, formulations) that involves crosslinking of hair (human, non-human), wool, or other protein or keratin fibers using green and sustainable chemicals that can retain the curliness or straightness, once crosslinked. The new green technology is also very inexpensive since the raw materials such as sugars used are inexpensive. A particular embodiment of a process of the green technology of the present disclosure is briefly described below.

In short, the sugars such as sucrose are oxidized using benign oxidizing agent such as hydrogen peroxide ($H_2O_2$) to obtain aldehyde groups, see Ghosh-Dastidar, *Green Chemistry*, 15(11):3243-3251 (2013) and published International Patent Application No. PCT/US2013/073956 (Dec. 9, 2013), the disclosures of which are incorporated by reference herein. Many sugars (5 carbon, 6 carbon), dimers, trimers, tetramers, etc., including stachyose, raffinose, and many others can also be oxidized and used as crosslinker as long as at least two aldehyde groups can be obtained on a single molecule. When the oxidized sugar is diffused in the hair, the aldehyde groups can react with the amine groups in keratin (human hair, wool, etc.) in amino acids such as lysine, arginine and possibly histidine, crosslinking the molecules. Sugar oxidation can also create carboxyl (COOH) groups which may also react with hydroxyl (OH) or amine ($NH_2$) groups. However, aldehyde groups are preferred as they react very fast with the amine groups and in many cases, at room temperature. Once crosslinked, the hair can retain their existing shape. For example, if a flat-iron is used the crosslinking reaction can be completed to the fullest extent possible due to its high temperature and the resultant hair will be much straight and if hot rollers are used, curly hair can be obtained. Since the crosslinking is chemical covalent bonding, and hence permanent, hair straightness or curliness or fizz can be expected to be retained for a long time. If high degree of crosslinking is obtained, hair may be washed without changing their straight or curly state.

In the case of woolen fabrics, dry cleaning is commonly recommended. While this is because of the felting (shrinkage due to the locking of the scales present on the wool surface) that occurs in washing/drying process, particularly when machine dried, woolen fabrics easily wrinkle when washed. Crosslinking wool (or other protein based fibers), with oxidized sugars as explained earlier, could be expected to retain the creases after washing, removing the need for ironing. The green crosslinking process described herein and below would also work with fabrics made with wool and other animal fibers such as cashmere, mohair, camel hair, alpaca, vicuna, etc., as well as fur fibers and silk. The crosslinking can also be used to obtain fabric stiffness. In many cases woolen fabrics are enzyme treated to remove the scales preventing felting when washed. In such cases, the wrinkle resistant fabrics can be easily washed in water cutting the dry cleaning costs.

Additional Aspects and Embodiments of the Present Disclosure

The present disclosure relates to, inter alia, residual sugars (e.g., soy flour sugars) and/or sugar mixtures as crosslinkers for enhancing mechanical performance of protein fibers, including, without limitation, fibers such as woolen, hair, and other protein fibers for various uses. Enhanced mechanical performance can include, without limitation, improved tensile properties (e.g., increased tensile strength, increased Young's modulus, etc.).

The present disclosure also relates to, inter alia, a green technology for enhancing strength of wool fiber using a soy flour sugar-based 'green' crosslinker.

In one aspect, a main goal of this disclosure and research was to crosslink protein (keratin) in wool fiber using a natural 'green' crosslinker formulated using soy flour sugars (SFS) and enhance the tensile properties. SFS, extracted from SF, was characterized, chemically modified and used as an inexpensive and non-toxic crosslinker for 'keratin', the protein in wool. The sugars in SFS were oxidized (OSFS) using sodium periodate ($NaIO_4$) to obtain aldehyde groups on them. Oxidation of sugar mixture in SFS produces multiple lengths of oxidized sugars containing aldehyde groups. While the high number of functional (aldehyde) groups obtained can provide chemical reaction with majority of the amine groups in keratin, the presence of different sugars, i.e., different molecular lengths, improves the possibility of reaching all reactive sites in keratin. These reactions lead to formation of both inter-molecular as well as intra-molecular linkages in the proteins forming a crosslinked system. The effect of chemical crosslinking on the performance properties of the wool fibers such as tensile properties were studied.

In one embodiment, a sugar mixture was obtained as a by-product from soy flour purification process with no significant value was oxidized to obtain multiple aldehyde groups. The oxidization was achieved using sodium periodate (NaIO4). The oxidized sugar mixture was used to crosslink wool fibers. The crosslinking increases the wool fiber strength by over 35%, Young's modulus (stiffness) by 56% and reduces moisture absorption. The increased properties of wool fibers could increase wool fiber spinning and weaving efficiencies. This can reduce significant amount of waste from these processes. In addition, this will allow spinning finer yarns from the same wool fibers, significantly increasing their value.

In certain aspects and embodiments, the rings of the composition of the present disclosure are fully (100%) opened, which is unique as compared to the prior art. Moreover, in certain aspects and embodiments of the composition of the present disclosure, the ratio of aldehyde per saccharide unit could be $\geq 1$, $>1$, $>1.5$, or $\geq 2$, which is an improvement over the prior art.

Various aspects and embodiments of the present disclosure can be implemented using methods, techniques, materials, and systems as described in WO 2015/168662-A1, entitled "Green Technology for Crosslinking Protein Molecules for Various Uses," published Nov. 5, 2015, the disclosure of which is hereby incorporated by reference herein in its entirety.

In one aspect, the present disclosure provides a method of crosslinking protein fibers. The method involves: (i) providing a crosslinking agent comprising an oxidized sugar mixture comprising a plurality of different oxidized sugars of different molecular lengths and having at least two aldehyde groups; and (ii) infiltrating a plurality of non-crosslinked protein fibers with the crosslinking agent under conditions effective to cause protein molecules contained in the non-crosslinked protein fibers to become crosslinked, thereby yielding a population of crosslinked protein fibers, wherein the protein molecules of the non-crosslinked protein fibers comprise amine groups that react with the aldehyde groups of the oxidized sugars to achieve the crosslinking of the protein molecules to yield the crosslinked protein fibers.

In one embodiment, the infiltrating step is carried out at a temperature and for a length of time sufficient to yield crosslinked protein fibers having improved tensile properties selected from the group consisting of increased tensile strength and increased Young's modulus compared to the non-crosslinked protein fibers. As used herein, increased tensile strength can include, without limitation, an increase of at least 20 percent, at least 25 percent, at least 30 percent, or at least 35 percent. As used herein, increased Young's modulus can include, without limitation, an increase of at least 20 percent, at least 25 percent, at least 30 percent, at least 35 percent, at least 40 percent, at least 45 percent, at least 50 percent, at least 55 percent, or at least 60 percent.

In one embodiment, the temperature used in the infiltrating step is selected from the group consisting of less than 160° C., less than 155° C., less than 150° C., less than 145° C., less than 140° C., less than 135° C., less than 130° C., less than 125° C., less than 120° C., less than 115° C., less than 110° C., less than 100° C., less than 90° C., less than 80° C., less than 70° C., less than 60° C., less than 50° C., less than 40° C., less than 30° C., and less than 20° C.

In one embodiment, the temperature used in the infiltrating step is between about 130° C. and about 160° C. for a period of time of between about 15 minutes and 25 minutes.

In one embodiment, the temperature is increased above room temperature by heating that is carried out by applying a source of heat during the infiltrating step.

A suitable source of heat can include, without limitation, a flat iron, hot rollers, a hot plate, a curling iron, a hair dryer, an iron, a clothes dryer, and an oven.

In one embodiment, the method further involves washing the population of crosslinked protein fibers to remove residual crosslinking agent or to remove crosslinking agent adhering to the protein fibers, thereby substantially removing the crosslinking agent.

In a particular embodiment, the washing is carried out using water or soap water.

In certain embodiments, the protein fibers are keratin-containing fibers. More particularly, the keratin-containing fibers can be, without limitation, animal fibers selected from the group consisting of wool, alpaca, angora, fur, cashmere, mohair, and qiviut. In certain other embodiments, the keratin-containing fibers can be, without limitation, animal fibers from animals selected from the group consisting of sheep, vicuna, alpaca, llama, muskox, goats, bison, camel, yak, horse, chinchilla, and rabbit. More particularly, the keratin-containing fibers can be, without limitation, animal fibers having a form selected from the group consisting of raw fibers, yarns, felts, and woven or knitted fabrics.

In one embodiment, the sugars are selected from the group consisting of monosaccharides, disaccharides, trisaccharides, tetrasaccharides, and oligosaccharides.

In another embodiment, the oxidized sugar mixture comprises oxidized soy flour sugars (OSFS) having sugars selected from the group consisting of fructose, glucose, sucrose, raffinose, and stachyose.

In another embodiment, the oxidized soy flour sugars are in their respective closed-chain form, open-chain form, or both closed- and open-chain form. More particularly, the open-chain form can be partially or fully open.

In another embodiment, the sugars have a ratio of aldehyde per saccharide unit of $\geq 1$, $>1$, $>1.5$, or $\geq 2$.

In certain embodiments, the crosslinking agent can be prepared according to a method involving the steps of: (i) providing a mixture of non-oxidized sugar molecules comprising a plurality of different sugars of different molecular lengths; and (ii) reacting the non-oxidized sugar molecules with an oxidizing agent comprising sodium periodate ($NaIO_4$) to cause oxidation of the non-oxidized sugar molecules to yield a reaction mixture comprising an oxidized sugar mixture comprising a plurality of different oxidized sugars of different molecular lengths and having at least two aldehyde groups, said oxidized sugar molecules corresponding to the crosslinking agent.

In one embodiment, the oxidation is carried out at room temperature.

In another embodiment, this method can further involve introducing barium chloride ($BaCl_2$) to the reaction mixture to inhibit further oxidation of the sugar molecules.

In another embodiment, this method can further involve removing residual amounts of the oxidizing agent after introducing the barium chloride ($BaCl_2$).

In certain embodiments, the crosslinking agent can include, without limitation, an oxidized soy flour sugars (OSFS) mixture having a pH of about 3.

In another aspect, the present disclosure provides a method of making a crosslinking formulation for crosslinking protein fibers. This method involves: (i) providing a mixture of non-oxidized sugar molecules comprising a plurality of different sugars of different molecular lengths; and (ii) reacting the non-oxidized sugar molecules with an oxidizing agent comprising sodium periodate ($NaIO_4$) to cause oxidation of the non-oxidized sugar molecules to yield a crosslinking formulation comprising an oxidized sugar mixture comprising a plurality of different oxidized sugars of different molecular lengths and having at least two aldehyde groups, wherein said mixture of oxidized sugars are crosslinking agents effective to react with amine groups of protein molecules contained in non-crosslinked protein fibers to yield a population of crosslinked protein fibers.

In one embodiment of this method, the oxidation is carried out at room temperature. In another embodiment, this method can further involve introducing barium chloride ($BaCl_2$) to the reaction mixture to inhibit further oxidation of the sugar molecules. In another embodiment, this method can further involve removing residual amounts of the oxidizing agent after introducing the barium chloride ($BaCl_2$). In certain embodiments, the crosslinking agent can include, without limitation, an oxidized soy flour sugars (OSFS) mixture having a pH of about 3.

In another aspect, the present disclosure provides a crosslinking formulation produced according to the above method. This crosslinking formulation includes an oxidized sugar mixture having a plurality of different oxidized sugars of different molecular lengths and having at least two aldehyde groups, where the mixture of oxidized sugars include crosslinking agents effective to react with amine groups of protein molecules contained in non-crosslinked protein fibers to yield a population of crosslinked protein fibers In another aspect, the present disclosure provides a method of treating animal fibers to improve their tensile properties. This method involves: (i) providing a crosslinking formulation according to the present disclosure; and (ii) treating a population of non-crosslinked animal fibers with the crosslinking formulation so as to yield a population of crosslinked animal fibers having improved tensile properties as compared to the population of non-crosslinked animal fibers, wherein the population of non-crosslinked animal fibers comprises non-crosslinked animal protein fibers having protein molecules having amine groups that react with the aldehyde groups of the different oxidized sugars of the crosslinking formulation.

In one embodiment, the treating involves infiltrating a plurality of non-crosslinked animal protein fibers with the crosslinking formulation under conditions effective to cause protein molecules contained in the non-crosslinked animal protein fibers to become crosslinked, thereby yielding a population of crosslinked animal protein fibers, wherein the protein molecules of the non-crosslinked animal protein fibers comprise amine groups that react with the aldehyde groups of the oxidized sugars to achieve the crosslinking of the protein molecules to yield the crosslinked animal protein fibers.

In one embodiment, the infiltrating step is carried out at a temperature and for a length of time sufficient to yield crosslinked protein fibers having improved tensile properties selected from the group consisting of increased tensile strength and increased Young's modulus compared to the non-crosslinked protein fibers. As used herein, increased tensile strength can include, without limitation, an increase of at least 20 percent, at least 25 percent, at least 30 percent, or at least 35 percent. As used herein, increased Young's modulus can include, without limitation, an increase of at least 20 percent, at least 25 percent, at least 30 percent, at least 35 percent, at least 40 percent, at least 45 percent, at least 50 percent, at least 55 percent, or at least 60 percent.

In one embodiment, the temperature used in the infiltrating step is selected from the group consisting of less than 160° C., less than 155° C., less than 150° C., less than 145° C., less than 140° C., less than 135° C., less than 130° C., less than 125° C., less than 120° C., less than 115° C., less than 110° C., less than 100° C., less than 90° C., less than 80° C., less than 70° C., less than 60° C., less than 50° C., less than 40° C., less than 30° C., and less than 20° C.

In one embodiment, the temperature used in the infiltrating step is between about 130° C. and about 160° C. for a period of time of between about 15 minutes and 25 minutes.

In one embodiment, the temperature is increased above room temperature by heating that is carried out by applying a source of heat during the infiltrating step.

A suitable source of heat can include, without limitation, a flat iron, hot rollers, a hot plate, a curling iron, a hair dryer, an iron, a clothes dryer, and an oven.

In one embodiment, the method further involves washing the population of crosslinked protein fibers to remove residual crosslinking agent or to remove crosslinking agent adhering to the protein fibers, thereby substantially removing the crosslinking agent.

In a particular embodiment, the washing is carried out using water or soap water.

In certain embodiments, the protein fibers are keratin-containing fibers. More particularly, the keratin-containing fibers can be, without limitation, animal fibers selected from the group consisting of wool, alpaca, angora, fur, cashmere, mohair, and qiviut. In certain other embodiments, the keratin-containing fibers can be, without limitation, animal fibers from animals selected from the group consisting of sheep, vicuna, alpaca, llama, muskox, goats, bison, camel, yak, horse, chinchilla, and rabbit. More particularly, the keratin-containing fibers can be, without limitation, animal fibers having a form selected from the group consisting of raw fibers, yarns, felts, and woven or knitted fabrics.

In one embodiment, the sugars are selected from the group consisting of monosaccharides, disaccharides, trisaccharides, tetrasaccharides, and oligosaccharides.

In another embodiment, the oxidized sugar mixture comprises oxidized soy flour sugars (OSFS) having sugars selected from the group consisting of fructose, glucose, sucrose, raffinose, and stachyose.

In another embodiment, the oxidized soy flour sugars are in their respective closed-chain form, open-chain form, or both closed- and open-chain form. More particularly, the open-chain form can be partially or fully open.

In another embodiment, the sugars have a ratio of aldehyde per saccharide unit of $\geq 1$, $>1$, $>1.5$, or $\geq 2$.

In another aspect, the present disclosure provides a fabric comprising the treated animal fibers produced according to the above method.

EXAMPLES

The following examples are intended to illustrate particular embodiments of the present invention, but are by no means intended to limit the scope of the present invention.

Example 1

Oxidation of Sugar by Hydrogen Peroxide: The Process

Twenty (20) g sucrose was added into 150 mL distilled water in a 500-mL flask, stirred for 5 min to completely dissolve the sucrose, then 50 mL of hydrogen peroxide (30%) was added into solution, which made the final hydrogen peroxide concentration to be 7.5%. The oxidation reaction was performed at 60° C. for 12 hrs. These conditions may be varied depending on the needs. The oxidized sucrose was dried in oven at 50° C. for at least 2 days to obtain highly viscous liquid. In order to remove any residual hydrogen peroxide, oxidized sucrose can be re-dissolved and dried one or more times. The chemistry of sucrose oxidation is shown in FIG. 2.

As mentioned earlier, many sugars (5 carbon, 6 carbon), dimers, trimers, tetramers, etc., including stachyose, raffinose, and many others. It is, however, important to know that higher sugars such as dimers, trimers, tetramers, etc., may even be preferred since they can have more than one —OH groups that can be utilized for conversion to aldehyde groups.

Many of these sugars can also be obtained from natural sources such as defatted soy flour which contains up to 35% carbohydrates, mostly in the form of higher sugars. These can be obtained by simple filtration process where the protein can be insolubilized at their isoelectric point (around 4.5 pH) while dissolving the sugars which can be easily filtered. Oligomeric (small molecular weight) species of starches may also be oxidized. Particularly water soluble species could be useful in this process.

Example 2

Aldehyde Group Content Determination

Two grams of sample was dissolved in 100 mL distilled water in a 500-mL flask. The solution was adjusted to pH 3.2 with 0.5 N NaOH and 15 mL of hydroxylamine reagent was added. The flask was capped (using cork stopper) and placed in a 40° C. water bath for 4 hrs with slow stirring. The excess hydroxylamine was determined by rapidly back titrating the reaction mixture to pH 3.2 with standardized 0.5 N HCl. A blank (without oxidized sucrose) determination with only hydroxylamine reagent was performed in the same manner. The hydroxylamine reagent was prepared by first dissolving 30 g hydroxylamine hydrochloride in 100 mL of 5 N NaOH before the final volume was adjusted to 500 mL with distilled water.

Carbonyl group content was calculated as follows:

$$\text{Aldehyde content } (\%) = \frac{\left[ \begin{array}{c} \text{blank} - \text{sample)mL} \times \\ \text{acid normality} \times 0.028 \times 100 \end{array} \right]}{\text{sample weight in g (dry basis)}}$$

Table 1 presents the sucrose oxidation conditions used and their corresponding aldehyde contents obtained for three different processing conditions used. Different aldehyde content can be expected, when different conditions are applied, e.g. amount of sucrose, hydrogen peroxide concentration, reaction time and reaction temperature.

TABLE 1

Sucrose oxidation conditions and their corresponding aldehyde contents.

| | Treatment Conditions | Aldehyde Content (%) |
|---|---|---|
| A | 20 g sucrose in 200 mL 7.5% hydrogen peroxide, room temp, 12 hrs | 10.56 |
| B | 20 g sucrose in 200 mL 7.5% hydrogen peroxide, 60° C., 12 hrs | 7.7 |
| C | 20 g sucrose in 200 mL 15% hydrogen peroxide, room temp, 12 hrs | 9.45 |

Example 3

Hair Treatment and Characterization

Crosslinking of Human Hair (and Other Protein Fibers) Using Oven:

Human hair specimens cut to a length of 10 cm were used in this test. The hair pieces were washed with Tide detergent solution (0.36% concentration) and rinsed with continuous water for 3 min. Eight (8) g of oxidized sucrose was added to 125 mL beaker containing 50 mL of water. Different oxidized sucrose concentrations can be used as long as oxidized sucrose can be well diffused from solution into inner structure of the hair. Higher the amount of oxidized sucrose diffused inside hair, more the crosslinking achieved. This can lead to higher straightness of the hair (when treated with flat-iron) as well as increased retention in humid air. Concentrated sodium hydroxide solution was used to adjust pH to 11, soap washed hair specimens were immersed and stirred at 50° C. with stir speed of 70 rpm for 15 min, 30 min and 1 hr, separately, in 3 trials. Treated specimens were placed on a flat surface and straightened by hand (due to the adhesiveness of oxidized sucrose). Specimens maintained their straightness during drying process. Final curing was carried out at a higher temperature of 85° C. in an air circulating oven for 1 hr after which the specimens were washed in continuous water (tap water) and dried at RT in air. Specimens were conditioned by hanging vertically at 65% humidity and 21° C. (ASTM conditions).

Crosslinking of Human Hair (and Other Protein Fibers) Using Flat-Iron:

Small bundle of curly human hairs were used in this test. The hair bundles were washed with Tide detergent solution (0.36% concentration) and rinsed with continuous water for 3 min. Eight (8) g of oxidized sucrose was added to 125 mL beaker containing 50 mL of water. Concentrated sodium hydroxide solution was used to adjust pH to 11, soap washed hair specimens were immersed and stirred at 50° C. with stir speed at 70 rpm for 15 min, 30 min and 1 hr, respectively. Treated specimens were slowly flat-ironed for 10 times, and then specimens were washed in continuous water stream (tap water) and dried at RT in air. Specimens were conditioned by hanging vertically at 65% humidity and 21° C. (ASTM conditions).

Curly Index of Human Hair:

Curly index is defined as ratio of stretched length of hair to its length at rest (in the curly state). See Loussouarn et al., *Int'l J. Dermatology*, 46(s1):2-6 (2007), the disclosure of which is incorporated by reference herein.

Curly index was calculated as follows:

$$\text{Curly index} = \frac{\text{stretched length of hair}}{\text{relaxed length of hair}}$$

Ten hair specimens were used for measurement and their average was recorded.

Example 4

Woolen Fabric Treatment and Characterization

Washing (Purification) of Woolen Fabric:

Four (4) g of woolen fabric was immersed in 300 mL with 0.36% concentration of Tide detergent solution and raised the temperature to 60° C. and stirred for 30 min. Then the fabric was taken out of the solution and washed in 300 mL water for 5 min. The washing process was repeated for 4 times. The washed fabric was dried in an air circulating oven at 60° C. for one day.

Crosslinking of the fibers can retain their form and, hence, the fabric crease and enhance the wrinkle resistance. Crosslinking of the wool fibers can also make them slightly stiffer and as a result, the fabric stiffness may increase. This, however, can be taken as one of the confirming evidences of the crosslinking reactions.

Crosslinking of Woolen Fabric:

Three and a half (3.5) g of oxidized sucrose was added into 200 mL distilled water and the previously washed woolen fabric was immersed into the solution. The pH of the solution was adjusted to 7 using 0.5 N NaOH solution to neutralized carboxylic groups in the oxidized sucrose. Different concentration, as desired, may also be used. Higher concentration will result in higher crosslinking of the wool fibers. The chemistry of neutralization of oxidized sucrose is shown in FIG. 5. The purpose of neutralization is to avoid hydrolysis of peptide bond induced by acid environment, in other words, to retain the physical property of woolen fabric. However, mild acids do not affect the wool fibers. The mixture (neutralized oxidized sucrose solution+woolen fabric) was heated at 80° C. for 1 hr. After that the fabric was taken out of the solution. The fabric was hung vertically until there was no more dripping. The take up of the solution can be adjusted, as desired, through the solution concentration or pad and dry method. The fabric was then dried at 80° C. for 20 min and followed by 120° C. for 3 min. The unreacted residual solution was removed by washing the fabric in 300 ml water for 5 min. This washing process was repeated for 4 times.

Fabric Stiffness Test:

Stiffness of woolen fabric was measured by fabric stiffness tester. A typical apparatus is can be used. The test procedures are described by ASTM D1388. The woolen fabric was conditioned in ASTM standard environment of 21° C. and 65% relative humidity for 12 hrs before cutting the test specimens of 25 mm×200 mm dimensions. The specimen was placed on the stationary table and moved by hand in a smooth manner at approximately 120 mm/min (4.75 in/min) until the edge of the specimen touches the knife edge. The overhang length from the linear scale to the nearest 0.1 cm was recorded. Several readings were recorded to confirm the reproducibility.

Wash Durability Test:

Woolen fabric was immersed in 300 mL 0.36% Tide® detergent solution and temperature was raised to 60° C. and kept stirring for 15 min. Then the fabric was taken out of the solution and washed in 300 mL of water for 5 min. The washing process was repeated 4 times. The washed fabric was dried at 60° C. in an air circulating oven for one day.

Example 5

Human Hair Treatment: Results

Effect of Conditioning Duration on Curly Index of Treated Human Hair:

Oxidized sucrose treated human hairs (Brazilian curly hair) were conditioned, and the curly index was used to evaluate the durability of treatment. FIGS. 6A-6D show pictures of curly hair before and after treatments.

Figure 6A:
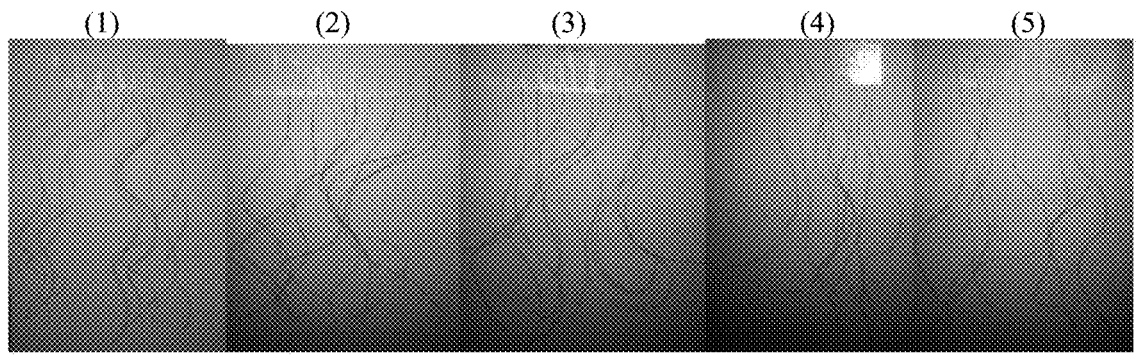
FIGS. 6A-6D are photographs of human hair before and after treatments with oxidized sugar.

FIG. 6A: Picture 1—'as received'; picture 2—soap water washed and air dried; picture 3—soap water washed, treated with oxidized sucrose solution for 10 min, oven cured at 85° C. for 1 hr, washed with continuous water and air dried; picture 4—soap water washed, treated with oxidized sucrose solution for 30 min, oven cured at 85° C. for 1 hr, washed with continuous water and air dried; picture 5—soap water washed, treated with oxidized sucrose solution for 1 hr, oven cured at 85° C. for 1 hr, washed with continuous water and air dried.

Figure 6B:
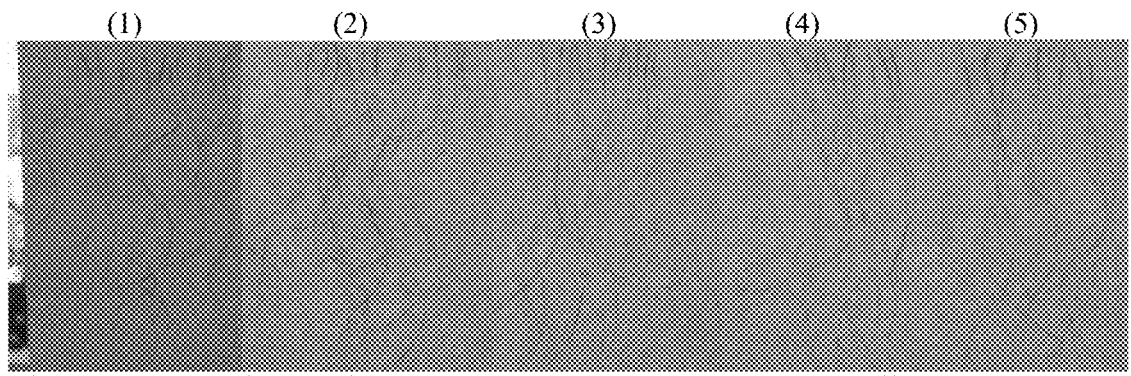

FIG. 6B: Picture 1—'as received' and conditioned for 4 days; picture 2—soap water washed, air dried and conditioned for 4 days; picture 3—soap water washed, treated with oxidized sucrose solution for 10 min, oven cured at 85° C. for 1 hr, washed with continuous water and air dried and conditioned for 4 days; picture 4—soap water washed, treated with oxidized sucrose solution for 30 min, oven cured at 85° C. for 1 hr, washed with continuous water and air dried and conditioned for 4 days; picture 5—soap water washed, treated with oxidized sucrose solution for 1 hr, oven cured at 85° C. for 1 hr, washed with continuous water and air dried and conditioned for 4 days.

Figure 6C:
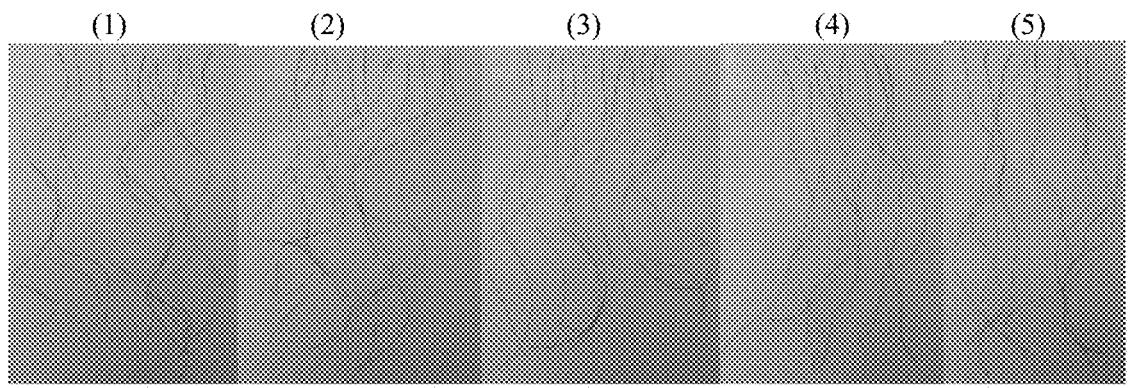

FIG. 6C: Picture 1—'as received' and conditioned for 8 days; picture 2—soap water washed, air dried and conditioned for 8 days; picture 3—soap water washed, treated with oxidized sucrose solution for 10 min, oven cured at 85° C. for 1 hr, washed with continuous water and air dried and conditioned for 8 days; picture 4—soap water washed, treated with oxidized sucrose solution for 30 min, oven cured at 85° C. for 1 hr, washed with continuous water and air dried and conditioned for 8 days; picture 5—soap water washed, treated with oxidized sucrose solution for 1 hr, oven cured at 85° C. for 1 hr, washed with continuous water and air dried and conditioned for 8 days.

Figure 6D:
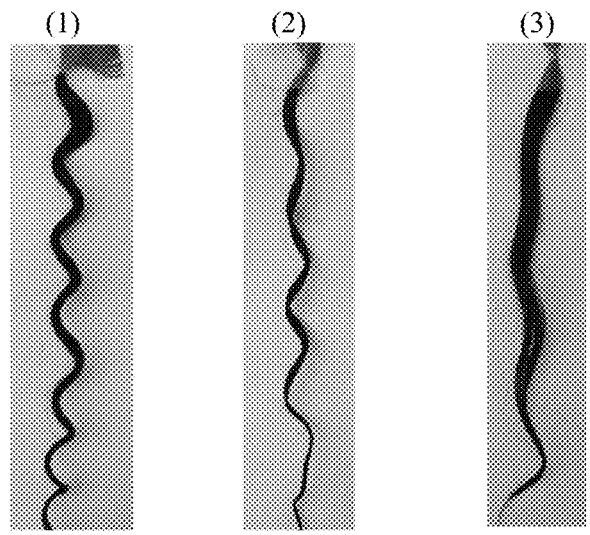

FIG. 6D: Picture 1—'as received'; picture 2—soap water washed and air dried; picture 3—soap water washed, treated with oxidized sucrose solution for 30 min, flat-ironed, washed with continuous water and air dried Curly indices of previously mentioned conditions were recorded and shown in Table 2.

TABLE 2

Curly index of specimens before and after conditioning*

| Specimen | Before conditioning | After 4 days conditioning | After 8 days conditioning |
|---|---|---|---|
| 1 | 1.21 | 1.26 | 1.29 |
| 2 | 1.33 | 1.39 | 1.39 |
| 3 | 1.12 | 1.19 | 1.22 |
| 4 | 1.05 | 1.06 | 1.06 |
| 5 | 1.08 | 1.08 | 1.08 |
| 6 | 1.09 | | |

*Specimen 1—'as received'; specimen 2—soap water washed and air dried; specimen 3—soap water washed, treated with oxidized sucrose solution for 10 min, oven cured at 85° C. for 1 hr, washed with continuous water and air dried; specimen 4—soap water washed, treated with oxidized sucrose solution for 30 min, oven cured at 85° C. for 1 hr, washed with continuous water and air dried; specimen 5—soap water washed, treated with oxidized sucrose solution for 1 hr, oven cured at 85° C. for 1 hr, washed with continuous water and air dried; specimen 6—soap water washed, treated with oxidized sucrose solution for 30 min, flat-ironed, washed with continuous water and air dried.

Based on the results from FIGS. 6A-6D and Table 2 we can conclude that oxidized sucrose treated hair is able to retain straightness at high humidity (65% RH) environment. Higher the value of curly index meaning the greater the curliness of hairs, a curly index of 1 can represent a completely straighten hair. Number 2 hairs (soap washed and air dried) show a larger curve diameter compared with as received curly hairs, which explains the fact that curly index of number 2 hairs is higher than number 1. This means the soap washed and air dried hairs have higher curliness than the 'as received' hairs (number 1). Number 4 and 5 hairs shown lower curly index compared with number 3 hairs, meaning that 30 min or 1 hr treatment of hair with oxidized sucrose solution result in better crosslinking reaction compared with 10 min treatment. After 4 days of conditioning, curly index of number 4, 5 hairs are close to those before conditioning, however, number 1,2,3 hairs undergo larger curly index increase, which indicates high humidity environment causes hair to become more curly. After 8 days of conditioning, curly index of number 1 hairs increase to 1.29, however number 2 hairs retain same hair curliness. Number 3 hairs (treated for 10 min with oxidized sucrose, cured in oven, washed in water and air dried) continue increasing in curly index which implies that hairs with 10 min oxidized sucrose treatment do not have sufficient crosslinking to retain straightness. No change in curly index was observed for number 4 and 5 hairs between 4 and 8 days of conditioning, indicating 30 min or longer oxidized sucrose treatment provides sufficient amount of crosslinking to retain straightness under high humidity environment.

Oxidized sucrose solution was used to crosslinking bundle of hairs as well. As shown in FIG. 6D, Hair specimens were treated with oxidized sucrose solution (prepared 40 days before test) for 30 min, flat-ironed 10 times, washed with sufficient amount of tap water and air dried. Curly index decreased from 1.21 ("as-received") to 1.09 (oxidized sucrose solution treated hairs), which indicates that the oxidized sucrose solution treated hairs can be further crosslinked using commercial flat-iron. Similar results were observed when hairs were cured by oven and flat-iron.

These results indicate that the 'Green' technology developed here of using oxidized sucrose to crosslink hair has been successful. Our results showed a significant improvement in hair straightness after treating with oxidized sucrose and straightness could be well maintained under high humidity environment. Further, crosslinking of oxidized sugar treated hairs can be achieved by using commercial flat-iron.

Example 6

Woolen Fabric: Results

Figure 7:
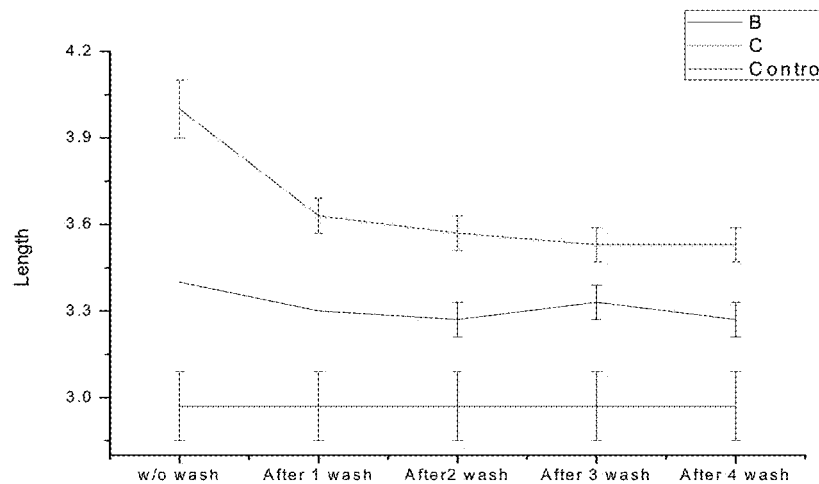
FIG. 7 is a graph showing crosslinked woolen fabric stiffness as a function of number of washes.

In the case of sucrose, the aldehyde content was higher when the reaction was carried out at room temperature, and the higher hydrogen peroxide concentration resulted in slight lower aldehyde content. Table 3 presents the stiffness of the control and the treated (crosslinked) woolen fabrics before and after up to 4 separate washings. FIG. 7 presents the crosslinked woolen fabric stiffness as a function of number of washes.

TABLE 3

Stiffness test results of woolen fabrics crosslinked using oxidized sucrose

| | w/o wash | After 1 wash | After 2 washes | After 3 washes | After 4 washes |
|---|---|---|---|---|---|
| B | 3.4 (±0) | 3.3 (±0) | 3.27 (±0.06) | 3.33 (±0.06) | 3.27 (±0.06) |
| C | 4 (±0.1) | 3.63 (±0.06) | 3.57 (±0.06) | 3.53 (±0.06) | 3.53 (±0.06) |
| Control | 2.97 (±0.12) | 2.97 (±0.12) | 2.97 (±0.12) | 2.97 (±0.12) | 2.97 (±0.12) |

The specimen B is the woolen fabric crosslinked by oxidized sucrose 'B' (as described in Table 1), and the specimen C is the wool fabric crosslinked by oxidized sucrose 'C'. For comparison, control (untreated) fabric stiffness has also been shown. There was no change in the stiffness of the untreated fabric after up to 4 washings. It is clear that the fabric stiffness corresponded with the aldehyde content in the oxidized sucrose. Fabric treated with oxidized sucrose 'C' showed significantly higher stiffness than the fabric treated with oxidized sucrose 'B'. After the first washing the stiffness reduced for both treated fabrics. However, after 4 washings the stiffness of both treated fabrics was much higher with treatment with 'C' much higher than treatment with 'B'. Also, it is clear from the data that the stiffness of the fabric treated with 'C' stabilized after 4 washings. It should be possible to increase the aldehyde content higher by simply increasing the concentration. This can give even better treatment results. It is expected that the crease retention will be higher for these fabrics as well.

From the results on hair and woolen fabrics discussed here, it may be concluded that the 'green' treatment developed here can be easily used for crease retention of woolen and other protein fibers.

Woolen Fabric Stiffness Crease resistance:

The results of the crease retention and wrinkle resistance tests and the related detailed processes are provided in FIGS. 9, 10, 11A-11B, 12A-12B, 13, 14A-14B, 15A-15B, 16, 17A-17B, 18A-18B, 19, 20, and 21A-21B. These tests clearly indicate that the woolen fabrics 1) retain crease after washing and 2) are not wrinkled after washing.

Example 7

Oxidization of Sucrose to Sucrose Aldehyde 40 g of sucrose was dissolved in 50 ml DI water. Then 50 ml of 30% hydrogen peroxide was added to the sucrose solution. Thus, the final concentration of the hydrogen peroxide used was 15%. This solution was kept in a bath at 60° C. with constant magnetic stirring at 200 rpm to carry out the oxidation of sucrose to get aldehyde groups. At the end of 6 hours, the solution was cooled down to room temperature. The pH of this mixture at this point was found to be 2±0.1. It was then adjusted to pH 6 using NaOH and heated to 50° C. 30 µl of catalase (GC 118, DuPont) was then added to the oxidized sucrose aldehyde solution at 50° C. to stop further oxidization of aldehydes into acids and stirred at 200 rpm for 10 minutes. Catalase catalyses the decomposition of hydrogen peroxide into oxygen and water. The pH was then adjusted to 10.5 using NaOH to treat the hair. FIG. 3 illustrates the scheme of oxidation of sucrose. A variety of catalases and peroxidases can be used.

Example 8

Hair Straightening Process

Figure 8:
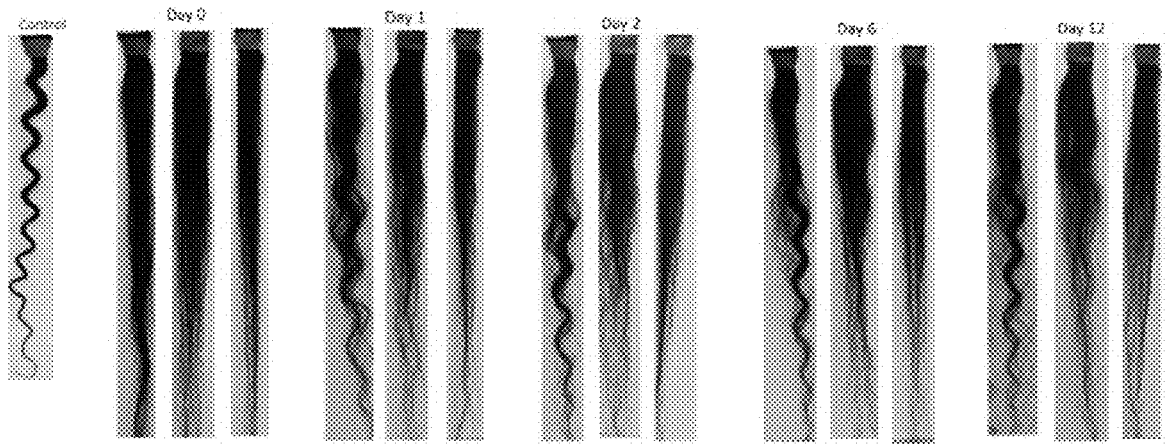
FIG. 8 is a photograph of hair treated with an oxidized sugar after various times and treatment with flat ironing.
Figure 9:
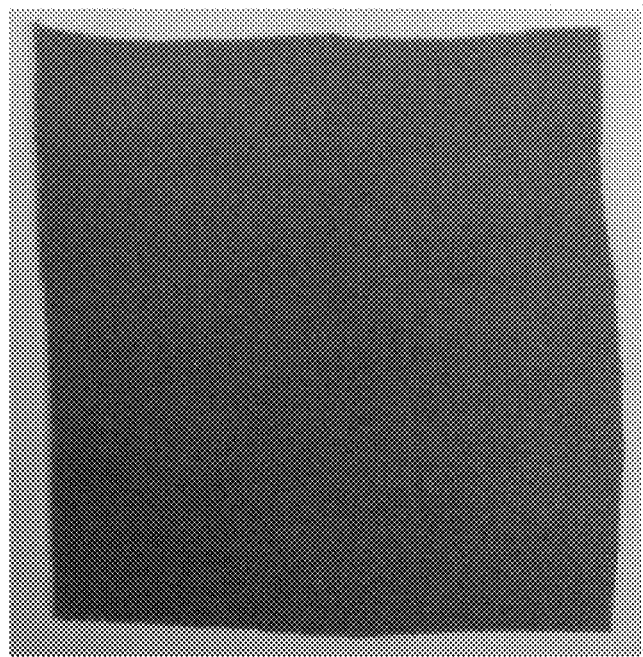
FIG. 9 is a photograph of woolen fabric "as-received" and before treatment.
Figure 10:
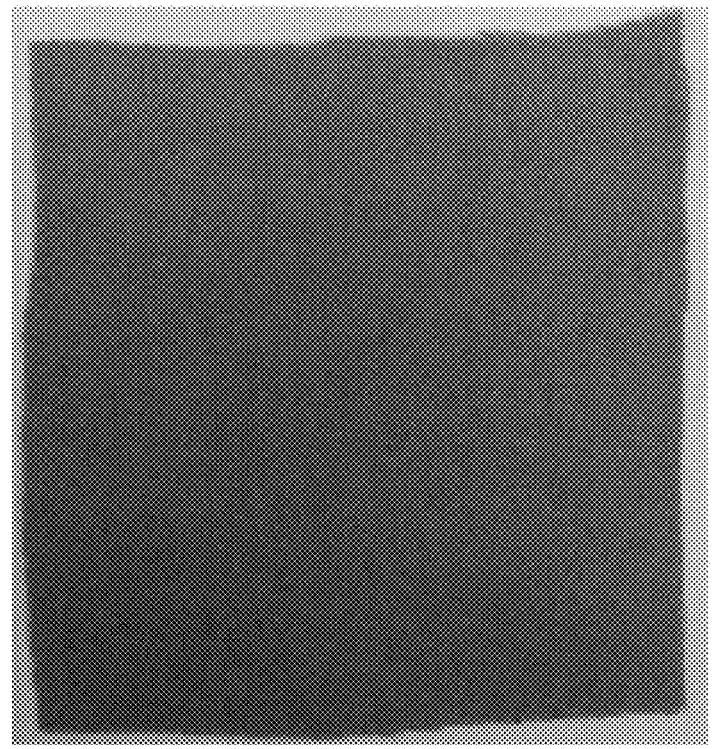
FIG. 10 is a photograph of a control woolen fabric (without any treatment). It is shown as ironed flat (ironed 5 minutes per side).
Figure 11A:
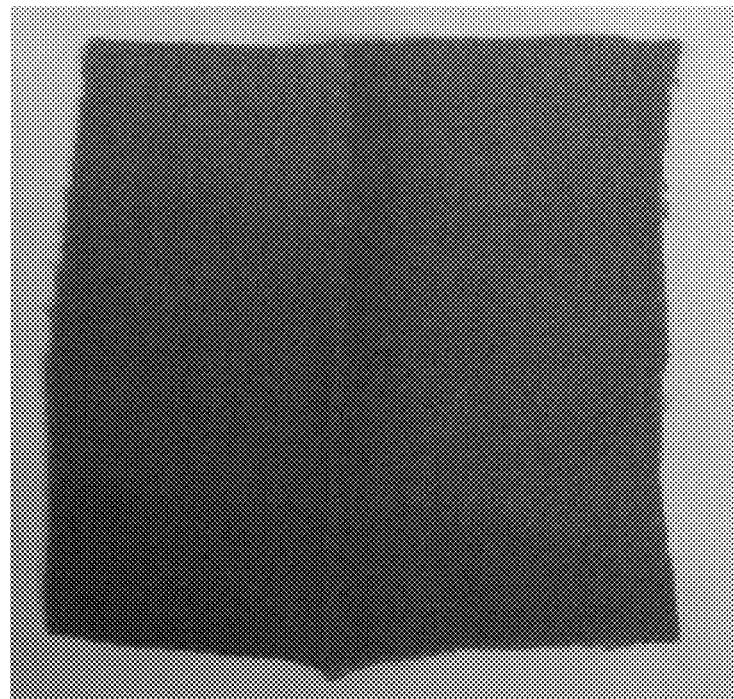
FIGS. 11A-11B are photographs of control woolen fabric (without any treatment). The fabric is ironed with a crease (folded in the middle, ironed 5 minutes per side).
Figure 11B:
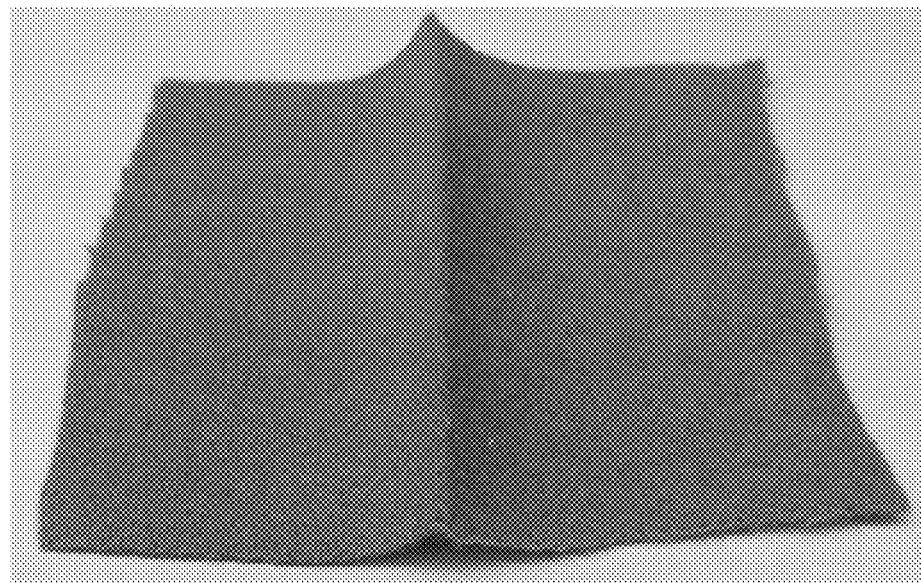
Figure 12A:
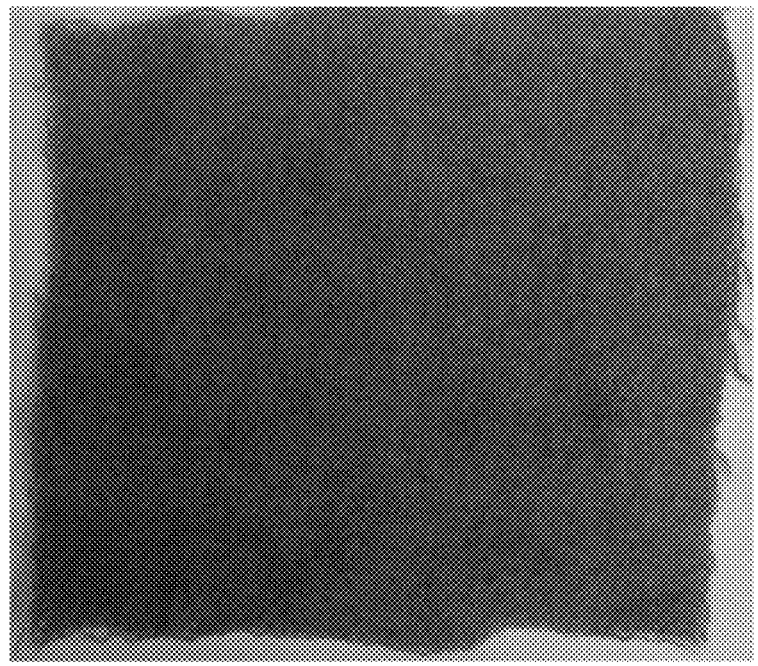
FIGS. 12A-12B are photographs of control woolen fabric (without any treatment). The fabric is (i) ironed with a crease (folded in the middle, ironed 5 minutes per side); (ii) washed with detergent (300 mL 0.36% Tide for 15 min, rinsed with large amount of water); and (iii) dried in an oven (80° C.). The fabric is wrinkled as all woolen fabrics do after regular washing.
Figure 12B:
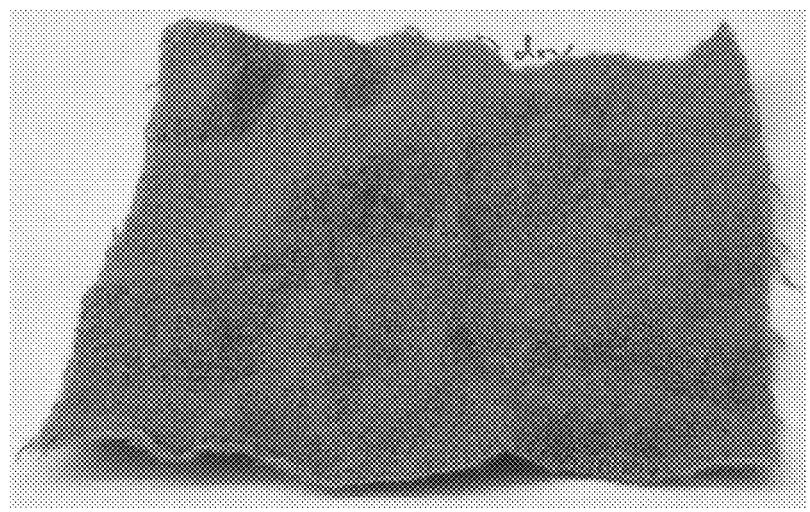
Figure 13:
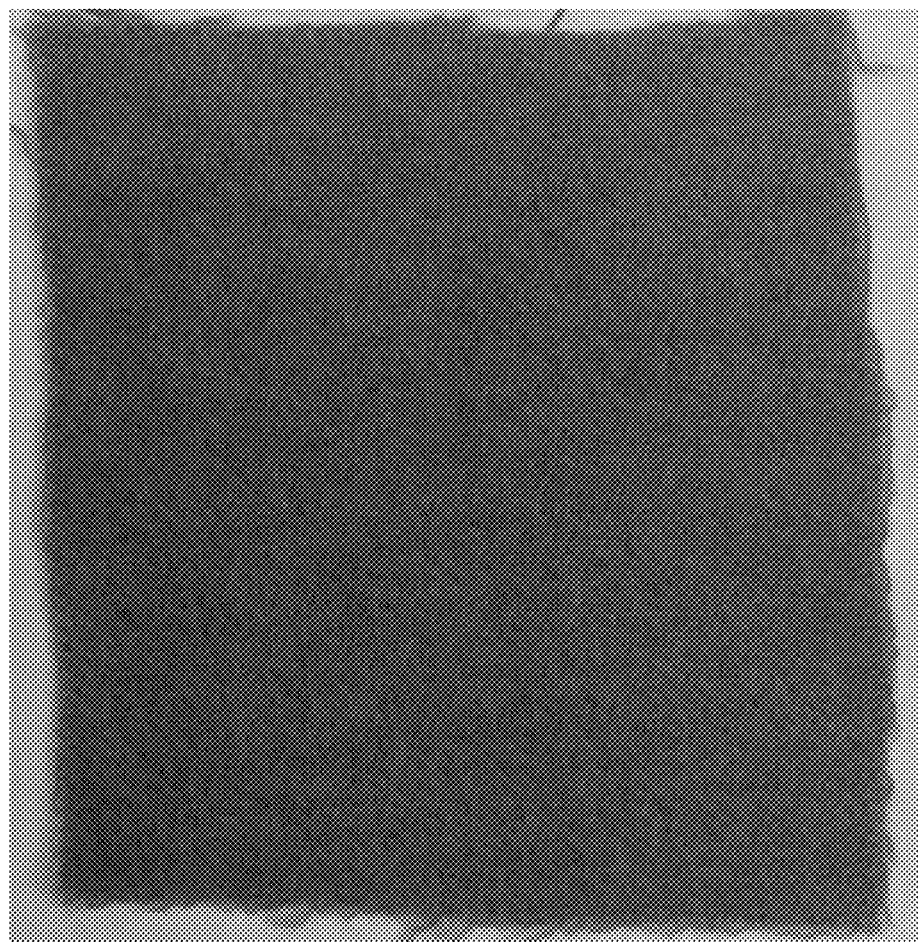
FIG. 13 is a photograph of a control woolen fabric (without any treatment). The fabric is (i) ironed with a crease (folded in the middle, ironed 5 minutes per side); (ii) washed with detergent (300 mL 0.36% Tide for 15 min, rinsed with large amount of water); (iii) dried in an oven (80° C.); and (iv) steam ironed flat (2 min. per side). The fabric is crease is lost.
Figure 14A:
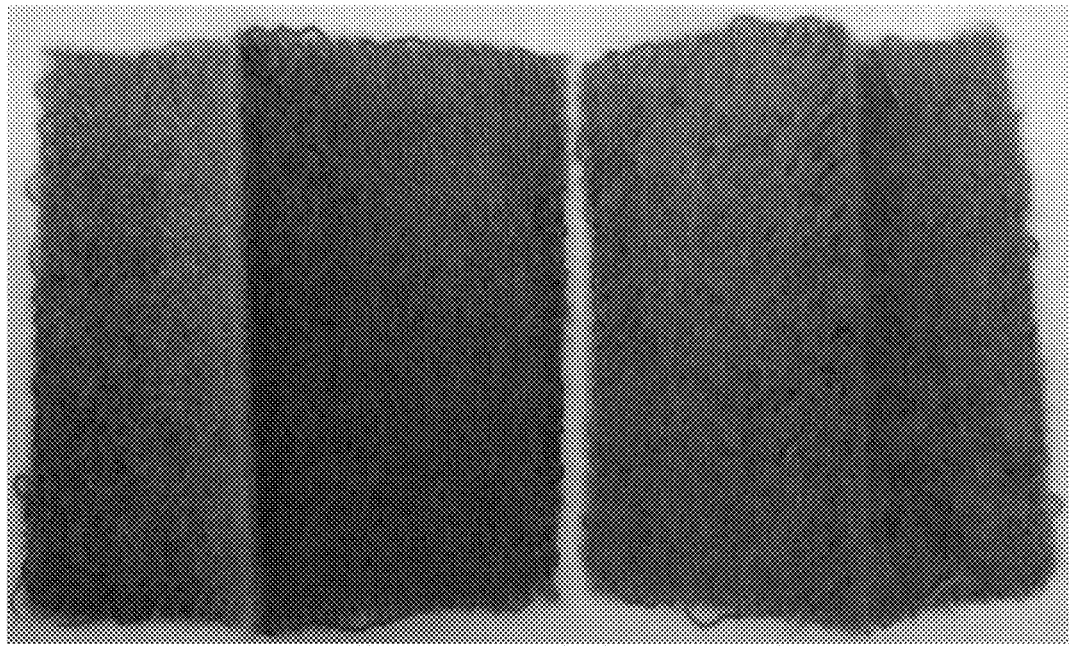
FIGS. 14A-14B are photographs of woolen fabric treated with oxidized sucrose solution. The fabric is ironed with a crease (folded in the middle, ironed 5 minutes per side). The creases in the treated fabric are shown.
Figure 14B:
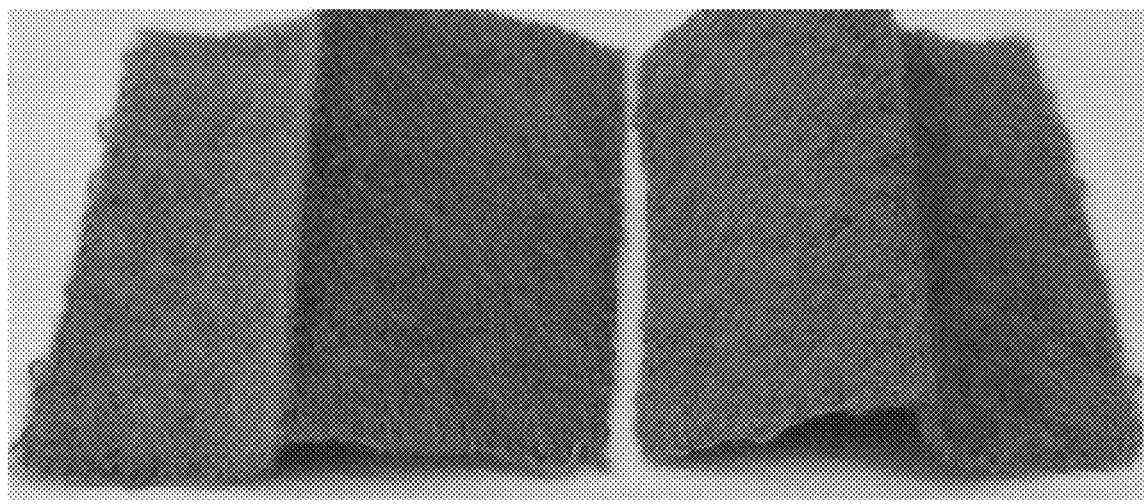
Figure 15A:
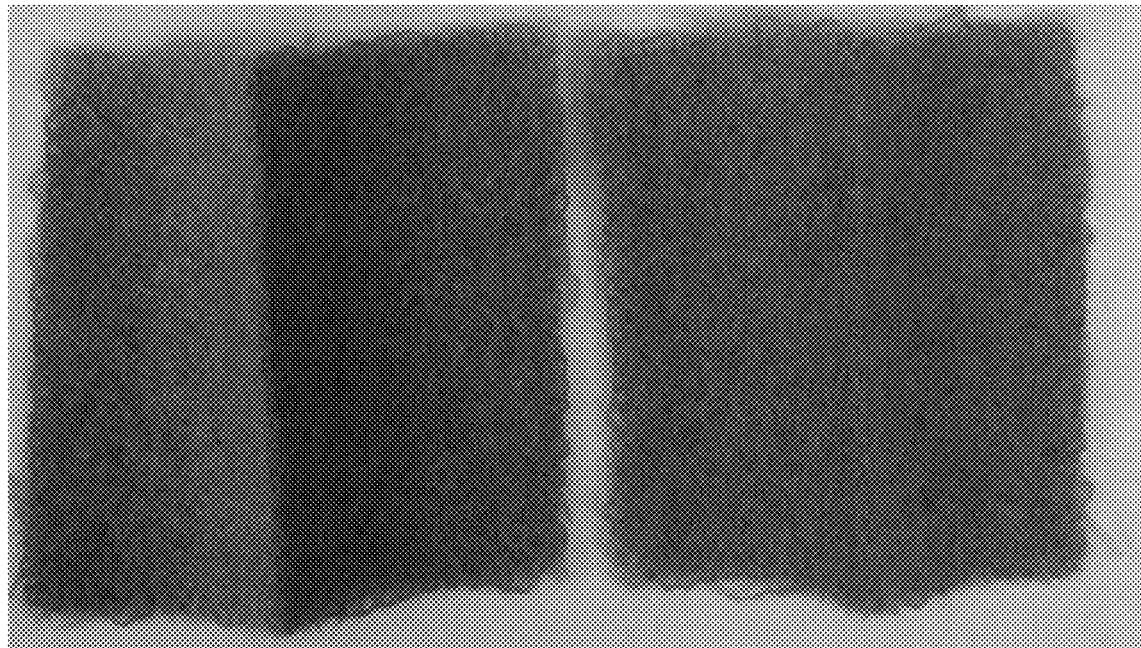
FIGS. 15A-15B are photographs of woolen fabric treated with oxidized sucrose solution. The fabric is (i) ironed with a crease (folded in the middle, ironed 5 minutes per side); (ii) washed with detergent (300 mL 0.36% Tide for 15 min, rinsed with large amount of water); and (iii) unfolded and dried in an oven (80° C.). Two views of the treated fabrics show the retained creases after washing the treated fabric specimens.
Figure 15B:
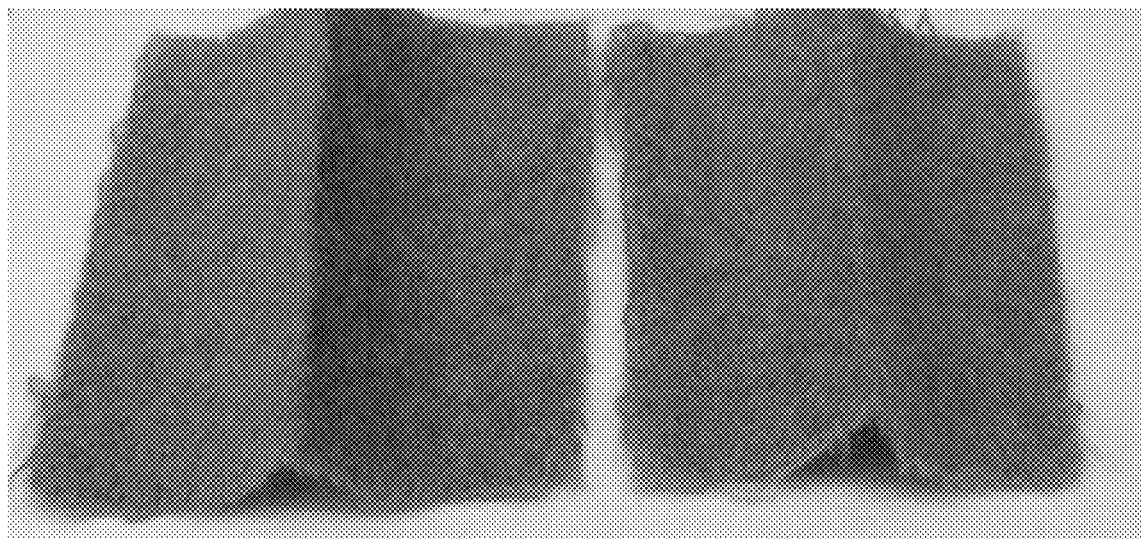
Figure 16:
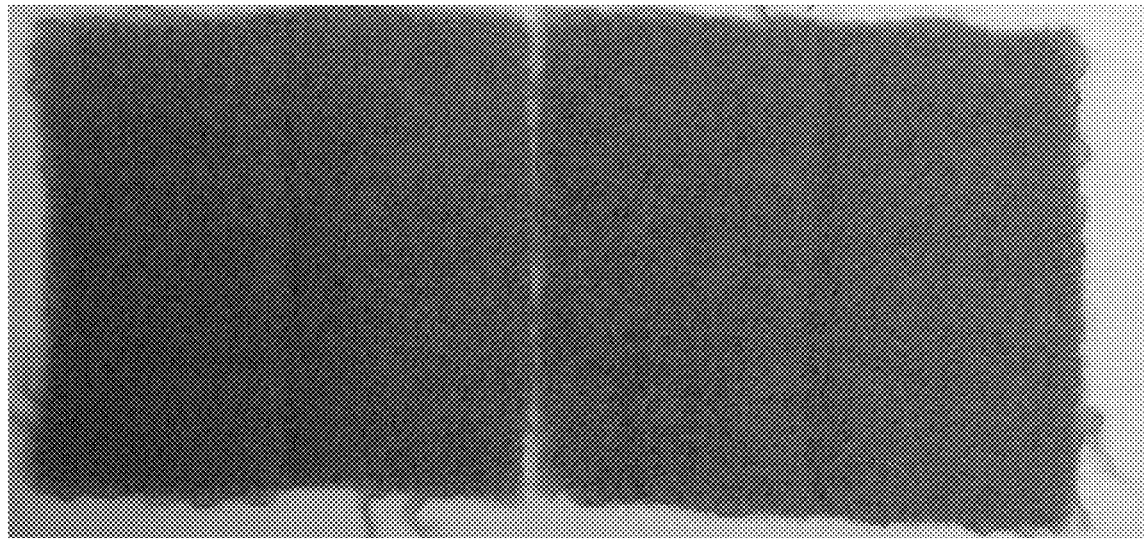
FIG. 16 is a photograph of a woolen fabric treated with oxidized sucrose solution. The fabric is (i) ironed with a crease (folded in the middle, ironed 5 minutes per side); (ii) washed with detergent (300 mL 0.36% Tide for 15 min, rinsed with large amount of water); (iii) unfolded and dried in an oven (80° C.); and (iv) steam ironed flat (2 min. per side). The fabric is shown to retain the creases even after washing and ironing flat.
Figure 17A:
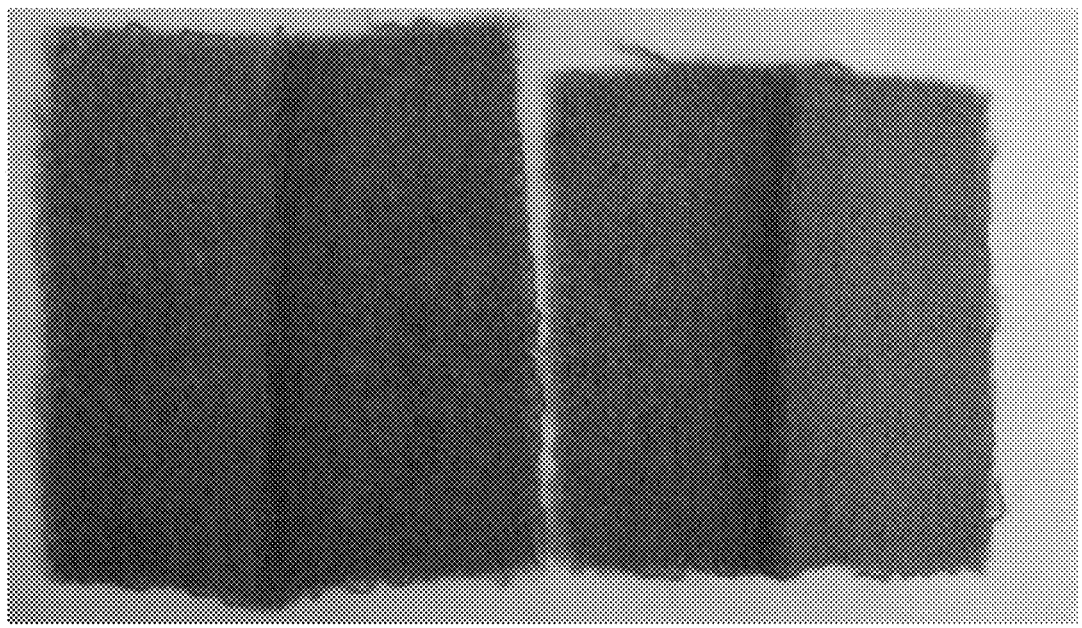
FIGS. 17A-17B are photographs of woolen fabric treated with oxidized sucrose solution. The fabric was oven cured at 120° C. with crease, obtained by placing the folded fabric between two glass plates for 15 min per side. Two views are shown for clarity. The fabric shows excellent crease after placing between flat glass plates at 120° C.
Figure 17B:
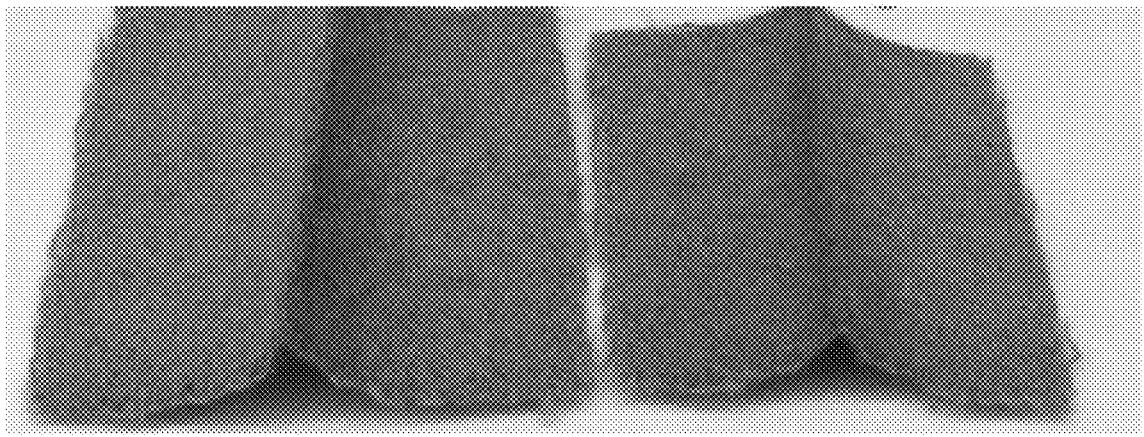
Figure 18A:
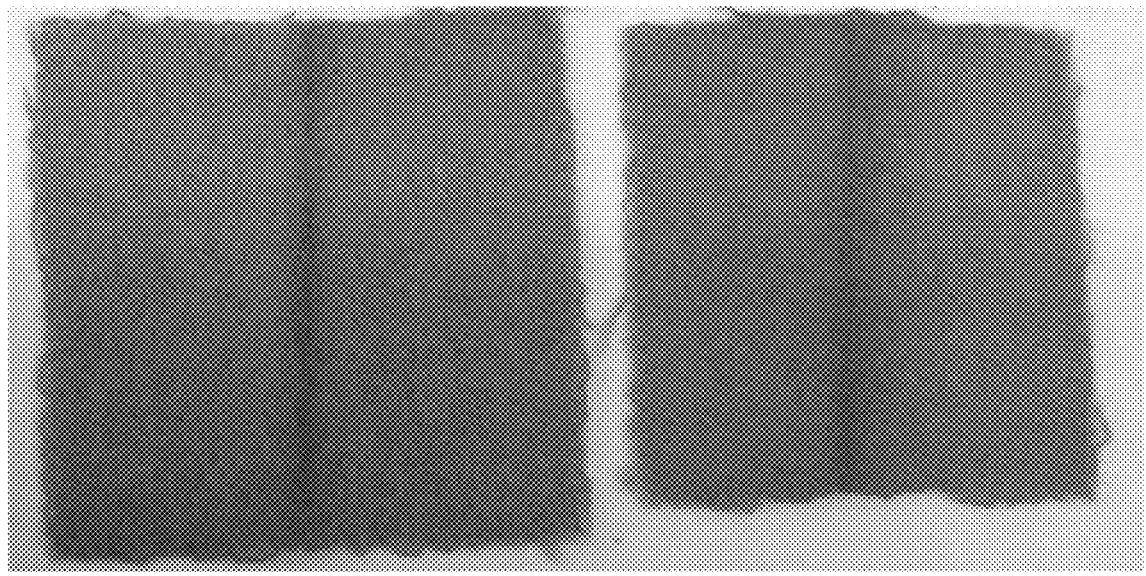
FIGS. 18A-18B are photographs of woolen fabric treated with oxidized sucrose solution. The fabric was (i) oven cured with crease (120° C. for 15 min per side, by placing the folded fabric between two glass plates); (ii) washed with detergent (300 mL 0.36% Tide for 15 min, rinsed with large amount of water); (iii) unfolded and dried in an oven (80° C.). The fabric retained creases even after washing with detergent and drying in an oven.
Figure 18B:
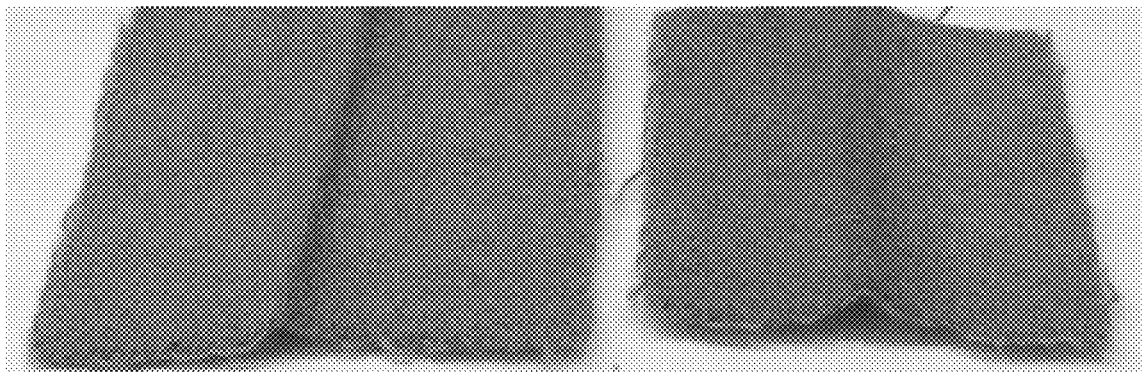
Figure 19:
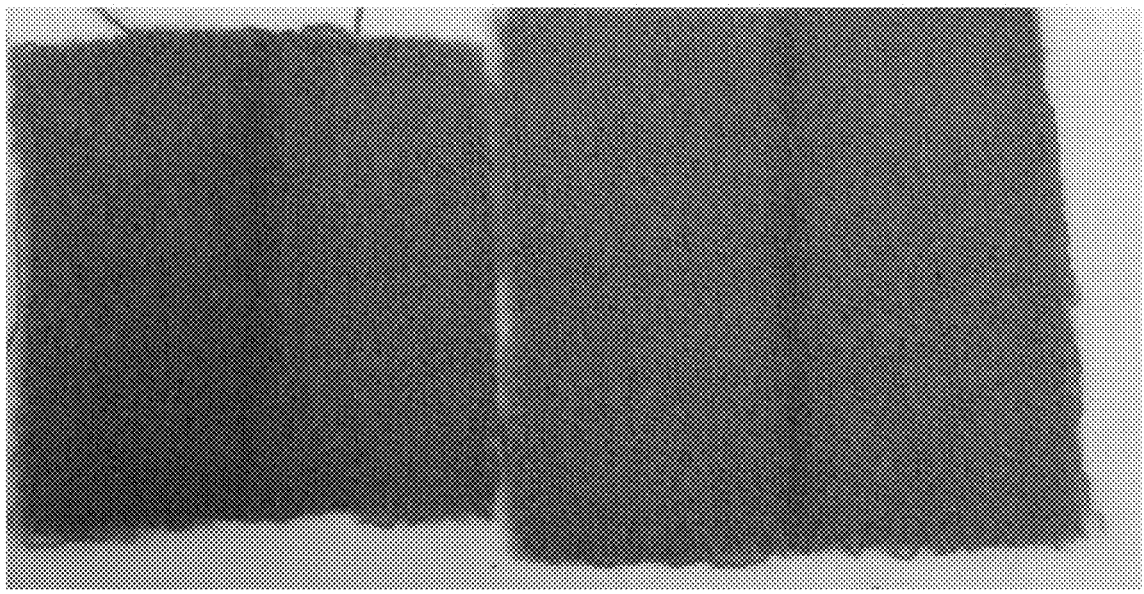
FIG. 19 is a photograph of a woolen fabric treated with oxidized sucrose solution. The fabric was (i) oven cured at 120° C. with crease by placing it in between two glass plates for 15 min per side; (ii) washed with detergent (300 mL 0.36% Tide for 15 min, rinsed with large amount of water)

About 12" long 100% virgin Brazilian natural curly human hair was used in this study. The stretched length of the curly hair was 16". It was first washed with Shampoo (Pantene) and water at room temperature and air dried. The prepared sucrose aldehyde solution was then heated to 50° C. and applied to the hair using a brush and ensuring that the solution is applied to all the hair and allowed to stand for 5 minutes. It was then flat ironed using a Remington flat iron for 5 passes and again coated with the sugar aldehyde solution using a brush. After, 15 min, it was flat ironed again for 10 passes and set aside for another 5 minutes before washing it with cold water to remove excess of the sucrose aldehyde on tha hair. It was then air dried and flat ironed for 5 passes. FIG. 8 illustrates various results of the process.

Example 9

Enhancing Strength of Wool Fiber Using Soy Flour Sugar-Based 'Green' Crosslinker Abstract This study presents, for the first time, the preparation and use of a 'green' crosslinker derived from waste soy flour sugar mixture (SFS) to crosslink keratin in wool fibers to increase its tensile properties. Earlier studies of keratin crosslinking involved chemicals such as glyoxal and glutaraldehyde that are toxic to humans. In addition, their effectiveness in improving tensile properties has been significantly lower than obtained in this study using modified SFS. Characterization of SFS using $^{13}C$ NMR revealed the presence of 5 sugars having different molecular lengths. Oxidation of SFS using sodium periodate resulted in multiple aldehyde groups as confirmed by $^1H$ NMR and ATR-FTIR. The oxidized SFS (OSFS) when used to crosslink the amine groups from the wool keratin resulted in 36% and 56% increase in the tensile strength and Young's modulus of the fibers, respectively. These significant increases in strength and Young's modulus were a result of having multiple aldehyde groups on each sugar molecule as well as different molecular lengths of sugars which favored crosslinks of multiple lengths between the α-helix microfibrils and within the cortical cell matrix of wool fibers. The crosslinking between the aldehyde groups in OSFS and amine groups in wool fibers was confirmed using ATR-FTIR and from the color change resulting from the Maillard reaction as well as decrease in moisture absorption by the fibers. Stronger wool fibers can not only increase the efficiencies of wool fiber spinning and weaving and reduce yarn and fabric defects but can also allow spinning finer yarns from the same fibers. Oxidized sugars with optimum molecular lengths can be used to crosslink other biological proteins as well, replacing the currently used toxic crosslinkers.

Results and Discussion

Characteristics of SFS.

$^{13}C$ NMR has been an important tool for the structural elucidation of carbohydrates.[16-17] FIG. 23 shows the $^{13}C$ NMR spectra of various sugars such as fructose, glucose, sucrose, raffinose, stachyose and the SFS obtained in this study. As seen in FIG. 23, all pure sugars showed chemical shifts between 60 ppm and 110 ppm.[17-19] Fructose and glucose are reducing monosaccharides consisting of six carbons each. The aqueous solutions of these monosaccharides consist of equilibrium mixtures of their tautomers.[20] In solution, fructose exists as an equilibrium of fructopyranose, fructofuranose, and other forms including acyclic structures.[20] Glucose exists in α and β pyranose together with their open chain forms.[19] The $^{13}C$ NMR spectra of fructose (FIG. 23, spectrum "a") and glucose (FIG. 23, spectrum "b") show more than six carbons because it shows tautomeric structures as they are present in aqueous solution.[20] Sucrose is a non-reducing disaccharide made up of fructose and glucose. $^{13}C$ NMR spectrum of sucrose is shown in FIG. 23 (spectrum "c"). The twelve carbons from sucrose are seen between 60 ppm to 110 ppm.[21] Raffinose is a non-reducing trisaccharide composed of galactose, glucose and fructose consisting of eighteen carbons as seen in its spectrum shown in FIG. 23 (spectrum "d"). Stachyose is also a non-reducing tetrasaccharide but consists of two galactose units, one glucose and one fructose units with a total of twenty four carbons as seen in its spectrum shown in FIG. 23 (spectrum "e"). Spectrum of SFS (FIG. 23, spectrum "f") shows chemical shifts between 60 ppm and 110 ppm as seen in all other sugars mentioned above, confirming the presence of different sugars in the SFS. Obendorf et al. have shown that the embryos of soybean seed accumulate sucrose, raffinose and stachyose during seed development and maturation.[22] Qiu and Netravali showed that SFS extracted from the same SF as in the present case, consisted of 21.21 g/L sucrose, 11.92 g/L stachyose, 1.92 g/L fructose and glucose (combined), 1.59 g/L raffinose, water and other compounds such as water soluble proteins using HPLC analysis.[14] Their data indicate that sucrose and stachyose are present in large amounts amongst all the sugars in SFS.[14] The $^{13}C$ NMR spectrum of SFS (FIG. 23, spectrum "f") shows all the chemical shifts present on sucrose and stachyose spectra (FIG. 23, spectra "c" and "e") confirming their presence in SFS.

Characteristics of SFS and OSFS.

FIG. 24A shows ATR-FTIR spectra of SFS and OSFS. The ATR-FTIR spectrum of SFS shows absorption peaks between 3700 $cm^{-1}$ to 2800 $cm^{-1}$ and 1700 $cm^{-1}$ to 900 $cm^{-1}$. The peaks between 1500 $cm^{-1}$ and 500 $cm^{-1}$ are characteristic peaks of the saccharide configurations as seen in sugars such as glucose, fructose, sucrose and others.[23] For example, the peak at 918 $cm^{-1}$ corresponds to C—H bending in the saccharides.[23] The peak at 997 $cm^{-1}$ is the characteristic peak of sucrose associated with the disaccharide linkage α-D-glucopyranosyl and β-D-fructofuranosyl groups.[24] The peaks at 1043 $cm^{-1}$ and 1250 $cm^{-1}$ correspond to the C—O stretch in the C—OH group of the saccharides while the peak at 1411 $cm^{-1}$ corresponds to the combination of —OH bending of C—OH group and C—H bending of alkenes.[23, 25] The peak at 3270 $cm^{-1}$ corresponds to the OH stretch from water.[25] The ATR-FTIR spectrum of SFS shows all the characteristic peaks present in saccharides confirming the presence of different sugars in it. The exact percentages of different sugars in SFS determined earlier by Qiu and Netravali using HPLC are presented in Table 4.[14] As seen from Table 4, sucrose and stachyose are present in considerable amounts in SFS, 58% and 32.5%, respectively, making over 90% of the total sugars. Fructose and glucose are reducing sugars and can exist in open-chain form in equilibrium forming aldehyde or ketone groups. Unlike monosaccharides such as fructose and glucose, sucrose, raffinose and stachyose are non-reducing sugars and do not exist in open-chain form, and, importantly, none of them have aldehyde groups. However, they can be oxidized to convert the hydroxyl groups to aldehyde groups. FIG. 22 presented earlier showed the proposed oxidation reaction of sucrose and stachyose. As seen in FIG. 22, $NaIO_4$ cleaves the vicinal diols and oxidizes the hydroxyl groups to aldehyde groups.[26] Sucrose and stachyose have five and eleven secondary hydroxyl groups, respectively, which form the vicinal diols that can be broken and oxidized to four and eight aldehyde groups, respectively (FIG. 22). Thus, oxidation of sucrose and stachyose forms polyaldehyde (tetra-aldehyde sucrose and octa-aldehyde stachyose) derivatives (FIG. 22). These aldehyde groups were confirmed through ATR-FTIR spectrum of OSFS as shown in FIG. 24A through the absorption peak at 1720 $cm^{-1}$. Similar peak at 1718 $cm^{-1}$ was seen by Jalaja and James after oxidizing sucrose using $NaIO_4$.[27] The peak intensities of both 1250 $cm^{-1}$ and 1411 $cm^{-1}$ which correspond to the C—OH bending in sugars are seen to reduce as a result of oxidation of hydroxyls to aldehyde groups.[23] Similarly, glucose, fructose and raffinose in SFS get oxidized to form aldehyde groups as well. Since these three sugars account for less than 10% of total sugars in the SFS solution, FIG. 22 presents only the sucrose and stachyose reactions. The formation of polyaldehyde was also confirmed from the $^1H$ NMR spectra. FIG. 24B shows the $^1HNMR$ spectra of SFS and OSFS. The spectrum of SFS shows characteristic sugar proton shifts at 5.4 ppm and between 4.2 ppm and 3.2 ppm.[28] The proton shift at 4.7 ppm is the solvent peak from $D_2O$. The proton shifts between 3 ppm and 4 ppm represent in —CH and —$CH_2$ in the sugars.[29] The proton shifts at 4 ppm and 4.2 ppm represent the protons from the vicinal diols of the sugars. The additional peak in OSFS at 8.3 ppm shows the formation of aldehyde groups upon oxidation of SFS. Liu et al. observed the free aldehyde peak upon oxidation of sucrose using $NaIO_4$ between 8 ppm and 8.5 ppm.[29] The additional small proton shifts seen between 5 ppm and 5.6 ppm show the formation of hemiacetals because of the intermolecular reaction between aldehyde and hydroxyl groups. Similar proton shifts were observed by Xu et al. and Liu et al. after oxidizing sucrose using $NaIO_4$.[26, 29] The change in pH of SFS from 5.5 to 3 after oxidation also confirms the presence of aldehyde groups in OSFS.

TABLE 4

Percent content of different sugars in SFS.[14]

| Fructose + Glucose | Sucrose | Raffinose | Stachyose |
|---|---|---|---|
| 5.24% | 57.90% | 4.33% | 32.53% |

Characteristics of Control and Crosslinked Wool Fibers.

FIG. 26A shows the ATR-FTIR spectra of control and crosslinked wool fibers. The spectrum for untreated (control) wool fiber shows a broad peak around 3268 $cm^{-1}$. This peak is assigned to O—H stretching from adsorbed water and N—H bending vibrations from the amide A linkages.[30] The peak at 2923 $cm^{-1}$ is due to $CH_2$ and $CH_3$ stretching vibrations while the peak at 1447 $cm^{-1}$ is due to C—H bending in protein. The spectrum for control wool fiber also shows three main characteristic peaks between 1700 $cm^{-1}$ and 1200 $cm^{-1}$. For example, the strong absorbance peak at 1628 $cm^{-1}$ is associated with the C═O stretch from the amide I linkages.[31] The medium strong absorbance peak at 1515 $cm^{-1}$ is assigned to N—H in-plane bending in amide II linkages.[31] The peak at 1233 $cm^{-1}$ is assigned to the C—N stretch of the amide III linkages.[30-31] The aldehyde groups of OSFS can react with the amine groups from keratin to form imine linkages as shown in FIG. 25. Oxidized sucrose present in OSFS has four aldehyde groups while stachyose, the longer molecule, has eight aldehyde groups and, in theory, all aldehyde groups can react with the amine groups present in keratin to form crosslinks. This crosslinking leads to the formation of imine linkages. It is, however, very difficult to see formation of new imine linkages in the crosslinked fibers due to spectral complexity of the proteins.[15, 32-34] FIG. 26B presents ATR-FTIR spectra of control and crosslinked wool fibers from 1800 $cm^{-1}$ to 1000 $cm^{-1}$. As can be seen in FIG. 26B, the spectrum of crosslinked wool fibers shows an additional small peak at 1040 $cm^{-1}$ which corresponds to the C—O stretch in C—OH as well as C—C stretch in the sugars.[23] This confirms the incorporation of OSFS within wool fibers. Similar additional peak at 1049 cm$^{-1}$ was observed after crosslinking soy proteins with oxidized sugars.[15] Jalaja and James observed a peak at 1030 cm$^{-1}$ corresponding to the C—O—C stretch of sugar moiety after crosslinking gelatin with oxidized sucrose.[27] The spectrum of crosslinked wool fibers in FIG. 26B also shows a small peak at 1341 cm$^{-1}$ which is not present in the spectrum of control wool fibers. This peak corresponds to the OH bending of the C—OH group and is present in sugars from SFS and confirms the presence of sugars after crosslinking.[23] It was observed that the amide II peak changed from the sharp and narrow peak to broad peak between 1510 cm$^{-1}$ to 1540 cm$^{-1}$ after crosslinking. Similar change in the amide II peak was observed when gelatin was crosslinked using glutaraldehyde.[35] The crosslinking reaction between primary amine groups in wool keratin with aldehydes from OSFS is through the formation of Schiff's base.[27, 36] The crosslinking of wool fibers can also be confirmed by the change in color and mechanical testing of the fibers. These results are discussed later.

Table 5 shows the L*, a*, b* values of control and crosslinked wool fibers. The change in color after Maillard reaction can be used to confirm crosslinking of proteins.[15, 32, 37] As shown in Table 5, the control fibers showed L*, a*, b* values of 78.02, −0.96, 3.80, respectively. Wool fibers crosslinked using OSFS (wool-OSFS) showed significant increase in the b* (yellowness) values. The b* value increased from 3.80 for control fibers to 5.31 and 8.64 after crosslinking with OSFS at 140° C. and 150° C. for 20 min, respectively. The increase in b* after treating with OSFS is another evidence of crosslinking reaction between the oxidized sugars and the amino acids from wool keratin. Higher b* value for wool-OSFS 150° C. (8.64) as compared to wool-OSFS 140° C. (5.31) is due to the increased extent of crosslinking with the increase in the temperature. Similar change in color was observed when dialdehyde starch was used to crosslink soy protein isolate.[37] Other dialdehyde sugars and aldehydes such as glutaraldehyde and glyoxal have also resulted in yellow/brown coloration after crosslinking the proteins present in wool, zein, gelatin, soy protein isolate, soy flour, collagen and other proteins, typical of the Maillard reaction.[15, 35, 37-41] Two types of browning have been observed after heating of sugars. First one is caramelization, caused by heating of sugars, which breaks down the molecules giving the yellow/brown color. The second is Maillard reaction, in which the browning is caused by heating reducing sugars in the presence of protein (amino groups). Reducing sugars in OSFS such as fructose and glucose contain aldehyde groups in the open chain form while non-reducing sugars such as sucrose, stachyose and raffinose contain aldehyde groups due to oxidation. The Maillard reaction between aldehyde groups in OSFS and amino groups in keratin causes the increase in the b* value. To confirm the change in color was due to Maillard reaction (and not caramelization), wool sliver was treated with pure SFS solution at 150° C. for 20 min. The pictures of the treated wool slivers are shown in FIG. 30 and as further described in Example 10. As can be seen from the FIG. 30 and in Table 5, the b* value of SFS treated wool (wool-SFS) sample is close to the pure wool sample, showing no evidence of caramelization. Thus, the increase in b* value for OSFS treated samples prove that the browning is due to Maillard reaction.[15, 37, 41] Crosslinking of wool using OSFS was restricted to 140° C. and 150° C. because caramelization of sugars and subsequent pyrolysis is prominent at temperatures above 160° C.[42]

TABLE 5

L*, a*, b* hunter color values of control and crosslinked fibers.

| Specimen | L* | a* | b* |
|---|---|---|---|
| Control | 78.02 ± 1.8 | −0.96 ± 0.02 | 3.80 ± 0.60 |
| Wool-SFS | 78.07 ± 2.1 | −0.98 ± 0.07 | 3.92 ± 0.98 |
| Wool-OSFS 140 | 72.82 ± 2.4 | −1.01 ± 0.03 | 5.31 ± 1.49 |
| Wool-OSFS 150 | 72.95 ± 2.3 | −1.02 ± 0.03 | 8.64 ± 3.01 |

FIG. 27 shows typical stress-strain plots of control and crosslinked wool fibers. As seen in FIG. 27, the stress-strain plots can be divided into three distinct regions: the initial Hookean region, yield region and the post yield (strain hardening) region. Tensile properties of control and crosslinked fibers are summarized in Table 3. As seen in FIG. 27, the initial Hookean region lies between 0%-3.4% strain for both control and crosslinked fibers. This region exhibits a linear relationship between stress and strain. Wool protein, in relaxed state, is called α-keratin wherein the keratin molecules are unstressed and in their natural helical shape. At low level of strain (~3.5%) the distortion involves extension of weaker bonds such as hydrogen bonding within the amino acids (seen in FIG. 25), Van der Waals forces, and coulombic interactions.[43] There is limited amount of movement of the chain segments and no phase change in the initial Hookean region. The folded α-helix structure of the fiber, hydrogen bonds between the helices, coulombic interactions due to side chains and some —COO$^-$ and —NH$_3^+$ groups oppose the distortion or strain. It was observed that the tensile stress of the fibers, at the end of the Hookean region, increased from 88 MPa to about 116 MPa, an increase of about 32%, after crosslinking with OSFS while the tensile strain reduced from 3.4% to 3.1%. Also, the Young's modulus of the fibers in the Hookean region increased from 2.5 GPa to 3.9 GPa, an increase of 56%, after crosslinking. Increases in tensile stress and Young's modulus values after crosslinking in the initial Hookean region were found to be statistically significant using unpaired t-test at a significance level of 0.05. The increase in the tensile stress and Young's modulus is clearly a result of the cross-links, particularly the shorter ones, formed within the microfibrils, macrofibrils and in the matrix region of the cortical cells of the wool fibers, that oppose the deformation. The microfibrils embedded within the matrix in the cortical cells are responsible for the strength of the fibers.[44] The Maillard reaction between aldehyde groups from OSFS and amine groups of the twisted keratin molecules creates intermolecular covalent bonding between the fibrils. This leads to an increase in tensile stress and modulus in the initial Hookean region after crosslinking. Beyond initial 3% strain, the strain increases rapidly for a small increase in the stress. This region is called the 'yield region'. The overall stress in the yield region increased from 88 MPa for control fibers to over 119 MPa, over 35% increase, for crosslinked fibers. At the same time the yield region which extended from 3.4% to 25.3% for control fibers changed to 3.1% to 21.7% for crosslinked fibers and the stress at the yield point increased from 117 MPa to 146 MPa. In the yield region, the α-helix chains unfold and phase transition, from α to β, occurs.[43] It has been demonstrated that at the end of yield region, 30% chains of α-helix chains unfold to β state.[43] This α to β transition is called the first order transition. The reduction in the tensile strain, from 25.3% for control to 21.7% for crosslinked fibers confirms the formation of inter- and intra-molecular linkages (crosslinks) between the peptide chains that restrict the molecular movement. The modulus in the yield region was also found to increase from 0.18 GPa to 0.27 GPa after crosslinking (50% improvement in the modulus). Beyond the yield region, the wool fibers stiffen para cortical cells which causes the crimp in the fiber. Absorbing less water could automatically reduce the undesired issues related to crimp.

TABLE 6

Tensile properties of the control and crosslinked fibers.

| Specimen | Diameter (μm) | Initial Hookean region | | | Yield region | | | Post Yield region | | |
|---|---|---|---|---|---|---|---|---|---|---|
| | | Stress (MPa) | Strain (%) | Modulus (GPa) | Stress (MPa) | Strain (%) | Modulus (GPa) | Stress (MPa) | Strain (%) | Modulus (GPa) |
| Control | 19.5 ± 1.8 | 88.2 ± 30.4 | 3.4 ± 1.4 | 2.5 ± 0.8 | 119.8 ± 32.9 | 25.3 ± 5.1 | 0.18 ± 0.06 | 203.0 ± 40.8 | 47.4 ± 7.6 | 0.35 ± 0.12 |
| Crosslinked | 19.0 ± 1.3 | 136.8 ± 37.3 | 3.1 ± 1.3 | 3.9 ± 1.2 | 145.5 ± 50.3 | 21.7 ± 3.5 | 0.27 ± 0.12 | 276.0 ± 54.5 | 41.8 ± 5.9 | 0.53 ± 0.13 | rapidly. This region is called the post-yield region and the stiffening phenomenon is called strain hardening. The post-yield region terminates on the rupture of the fiber. As seen in FIG. 6, the strain hardening phenomenon in the post yield region is more prominent in the crosslinked fibers as compared to the control fibers. The tensile fracture stress of the fibers increased from 203 MPa to 276 MPa after crosslinking, about 36% increase. The tensile strain was found to reduce from 47.4% to 41.8% after crosslinking. The secant modulus for the strain hardening region increased from 0.35 GPa to 0.53 GPa (51.4% increase) after crosslinking. Unpaired t-test showed that the increase in the moduli for all the three regions after crosslinking of the fibers were statistically significant at the significance level of 0.05. As mentioned earlier, OSFS contains mixture of different sugars having aldehyde groups. The major sugars present in OSFS, sucrose and stachyose, form tetra-aldehyde and octa-aldehyde, respectively, with different molecular lengths. This makes it easy to form various inter- and intra-molecular crosslinks with the protein side chains and allows forming a better 3-dimensional network within the fiber leading to an increase in the tensile stress and modulus in all regions of the fiber stress-strain plots. Hassan et al. crosslinked wool fibers using four different crosslinkers and found that the tensile strength increased from 103 MPa to 111.7 MPa, 115.2 MPa, 116.2 MPa, and 122 MPa for the glyoxal, itaconic anhydride, naphthalene disulfonic acid and succinic anhydride crosslinked wool fibers, respectively.[45] They observed a maximum of 18.5% increase in the strength of the wool fibers after crosslinking with succinic anhydride.[45] As seen earlier, crosslinking of fibers with OSFS showed an increase of about 36% in the tensile strength (from 203 MPa to 276 MPa). This shows that the natural soy flour sugar based green crosslinker is more effective in improving tensile properties of wool fibers than all other toxic bifunctional aldehyde-based crosslinkers currently used.

Keratin fibers have a tendency to absorb moisture which plasticizes them and causes a decrease in Young's modulus.[44] The moisture content of the conditioned fibers reduced from 9.14% in control fibers to 6.6%, a decrease of about 28%, after crosslinking. As expected, the 3-dimensional network obtained by crosslinking creates a more compact structure that acts as a moisture barrier. Reduced moisture absorption is beneficial since it can reduce the effect of moisture on fiber tensile properties. The cortex of the wool fiber is composed of ortho and para cortical cells. The para cortical cells contain disulfide (S—S) crosslinks resulting from cystine amino acid whereas the ortho cortical cells do not have S—S covalent crosslinks allowing them to absorb more moisture as compared to para cortical cells. This results in ortho cortical cells to swell and lengthen more than Surface Characteristics of Control and Crosslinked Wool Fibers.

Figures 28A, 28B, 28C, 28D:
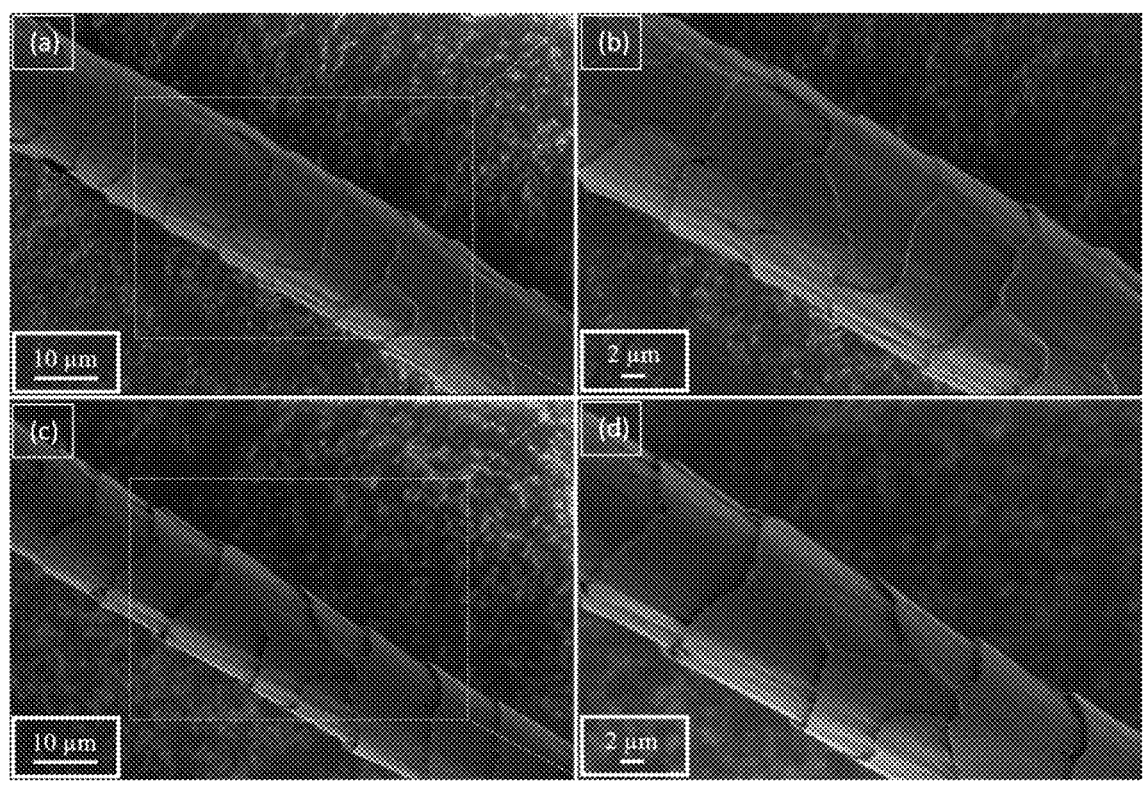
Figures 29A, 29B, 29C, 29D:
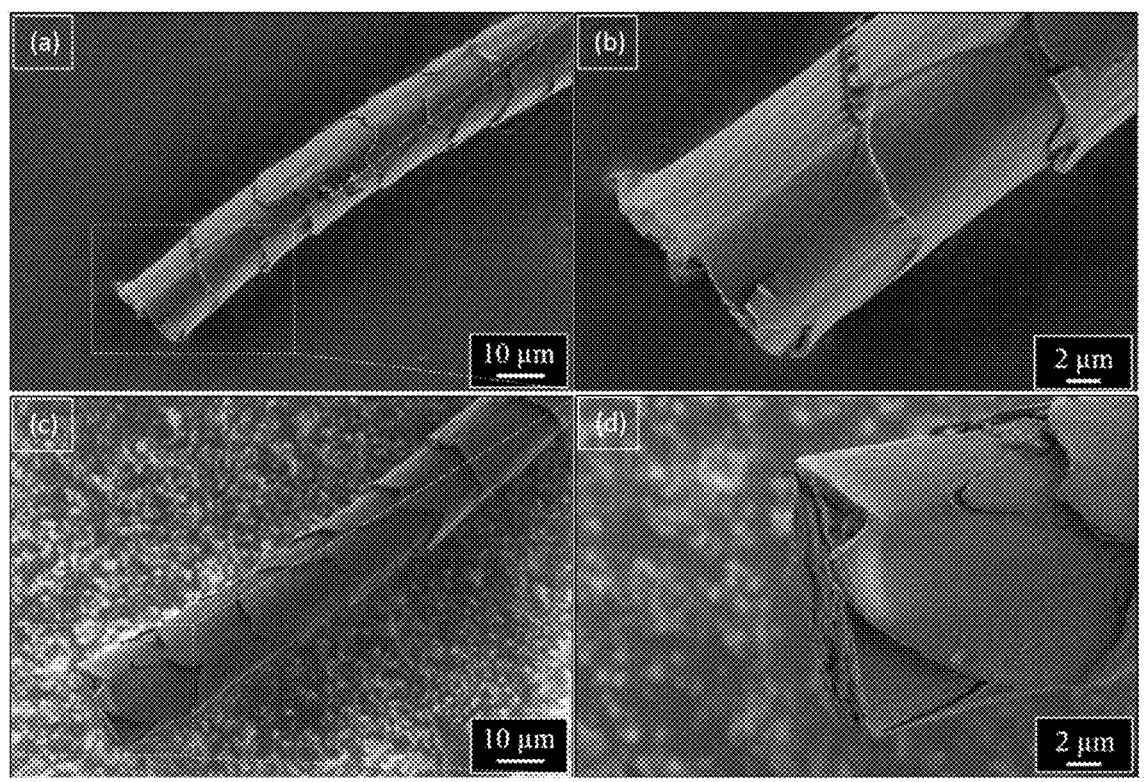

FIG. 28 shows SEM images of the surfaces of the control and crosslinked wool fibers taken at different magnifications. FIGS. 28A and 28B show control wool fibers with scales on the surface. These scales form the cuticle layer on the fiber surface.[46] FIGS. 28C and 28D show the surfaces of crosslinked fibers. When compared, the crosslinked fibers do not show any effect on the scalar structure of the fiber cuticle. No visible change or damage of scales can be observed after crosslinking the fibers with OSFS. Oxidized sugar molecules from OSFS are small molecules that can penetrate inside the cortex of the fiber and crosslink them internally, enhancing the tensile properties, while leaving the surface unchanged.

FIG. 29 shows SEM images of the fractured ends of control and crosslinked fibers taken at different magnifications. As seen in FIG. 29, the fracture surfaces of both control and crosslinked fibers show similar fracture characteristics. It can also be seen from the tensile plots of the fibers (FIG. 27) that the fibers do not fracture in stepwise fashion but undergo catastrophic failure after the strain hardening.

EXPERIMENTAL SECTION

Materials.

Wool fibers in sliver form and defatted soy flour (SF) were provided by Raymond Woolen Mills, India and Archer Daniels Midland Co., Decatur, Ill., respectively. Sodium periodate ≥99% and stachyose were purchased from Acros Organics, Bound Brook, N.J. Barium dichloride ($BaCl_2$) was bought from VWR, Rochester, N.Y. Glucose, fructose, sucrose and raffinose were purchased from Sigma-Aldrich. Analytical grade sodium hydroxide (NaOH) pellets and hydrochloric acid 37% reagent grade (HCl) were also purchased from Sigma-Aldrich Chemical Co., Allentown, Pa.

Extraction of Sugars from SF.

SF (65 g) was added slowly to 400 ml of DI water and stirred at 300 rpm at room temperature (RT) until a homogeneous SF mixture was obtained. The pH of the mixture was adjusted to 4.5 using HCl. At 4.5 pH, most of the amino acids present in the proteins from SF are at their isoelectric point and remain insoluble in water. The mixture was stirred overnight at 300 rpm at RT to dissolve all the sugars present in SF into water. The sugars were then filtered using a microfiber polyester fabric to remove the insolubilized protein from SF. The pH of the filtered solution containing the sugars was then adjusted to 5.5 using NaOH, stirred for 6 h at RT and filtered again to remove the small amount of remaining protein having amino acids with isoelectric point close to 5.5. The filtered solution containing soy flour sugars is termed as SFS. 250 ml of SFS was obtained after filtering twice. Assuming that we extract 30% residual sugars from the SF, the final concentration of sugars after filtration in SFS was close to 5%.

Oxidation of SFS.

Oxidation of SFS was carried out using $NaIO_4$. Different molar ratios (MR), 0.5 to 2.5 MR, of $NaIO_4$ to sugars were used to optimize the oxidizing reaction. (See FIG. 31 and the related discussion in Example 10 for optimization of reaction). The oxidation reaction was carried out in dark for 22 h at RT with gentle stirring at 200 rpm. At the end of the reaction, required amount of $BaCl_2$ was added to the solution to stop sugars from further oxidation (see FIG. 32 and the related discussion in Example 10). The solution was stirred for 5 min after addition of $BaCl_2$ and then placed at 4° C. for 1 h to allow complete precipitation of barium iodate $Ba(IO_3)_2$. It was then filtered to obtain the supernatant solution containing the mixture of oxidized SFS (OSFS). The pH of the prepared OSFS was found to be 3.

Wool Fiber Crosslinking.

Wool sliver, 7.5 inch long, was cut and immersed in flat form in the prepared OSFS solution for 10 min at RT in a rectangular Pyrex® box. After 10 min of immersion in OSFS, the sliver was taken out and gently squeezed to remove excess solution. The wet sliver was immersed flat again in the OSFS solution for 1 min at RT, taken out and gently squeezed again to ensure uniform wet pick-up by all fibers in the sliver with OSFS. The wet sliver was placed flat on a glass plate and cured in an air-circulation oven at 140° C. and 150° C. for 20 min to allow the crosslinking between aldehyde groups from OSFS and amine groups in wool keratin as shown later in FIG. 25. The sliver was flipped upside down after the half curing time (10 min) in oven to ensure uniform treatment to all fibers. The sliver was taken out and placed flat in a Pyrex® box containing DI water for washing. The crosslinked sliver was washed 2-3 times with water to remove all the unreacted sugars from the fiber surface. The crosslinked fibers in the sliver were dried and conditioned at ASTM conditions of 65±3% RH and 21±1° C. for 24 h prior to any testing.

Characterization of SFS, OSFS, Control and Crosslinked Wool.

A complete $^{13}C$ Nuclear Magnetic Resonance (NMR) analysis was performed to characterize SFS and various sugars present in SFS. The structural/chemical differences in SFS upon oxidizing were studied using $^1H$ NMR. $^{13}C$ and $^1H$ NMR spectra were recorded on an INOVA 400 spectrometer (Varian Inc., Palo Alto, Calif., USA) using $D_2O$ as the solvent for both.

Attenuated total reflectance Fourier-transform infrared (ATR-FTIR) analysis was done to characterize the effect of oxidation on SFS. ATR-FTIR was also used to study the crosslinking of wool. The ATR-FTIR spectra were collected using Thermo Nicolet Magna-IR 560 spectrometer (Madison, Wis.) having a split pea accessory. Each scan was an average of 300 scans from 4000 $cm^{-1}$ to 500 $cm^{-1}$ wavenumbers.

CIELAB color parameters of control and crosslinked wool fibers were measured using Macbeth Color-eye spectrophotometer, Model M2020PT, (Newburgh, N.Y.). The L*, a*, b* values stand for L*=0 (black) to L*=100 (white), -a* (greenness) to +a* (redness), and -b* (blueness) to +b* (yellowness). A standard value for the white calibration tile (L*=95.91 a*=-0.43 b*=1.01) was used to calibrate the spectrophotometer.

Tensile properties of single fibers were characterized using Instron universal testing machine, model 5566 (Instron Corp., Canton, Mass.). Single wool fibers were individually mounted on rectangular paper tabs and the two ends were secured using self-adhesive tape. The diameters of every single fiber was measured using a calibrated optical microscope, Olympus, model BX51 (Melville, N.Y.), at three different locations and the average was used to calculate the tensile properties of each fiber. The fibers were conditioned and tested at 65±3% RH and 21±1° C. at a gauge length of 20 mm and strain rate of 0.6 $min^{-1}$. Thirty single fibers were randomly chosen from different parts of the wool sliver of each type (control and crosslinked) for testing and statistical analysis. For the crosslinked fibers, ten fibers were chosen from each of the three different slivers treated at different times using OSFS solutions prepared at different times to ensure reproducibility of the results. Savitzky-Golay smoothening method was used to smoothen the tensile stress-strain plots[47]. Linear regression was performed on the smoothened plots to get accurate modulus values of the fibers. Unpaired t-test was used to test if the control and crosslinked fiber properties were statistically significant from each other.

To study the effect of crosslinking on the surface of the fibers and the fracture behavior of the control and crosslinked wool fibers, the surface and the fractured ends of the fibers fractured during the tensile tests were carefully mounted on standard aluminum stubs with double sided electrically conductive carbon tapes and characterized using Zeiss Gemini 500 scanning electron microscope, Germany, at 0.25 kV.

Conclusions

The present study has successfully demonstrated that the tensile performance of the wool fibers can be enhanced significantly using a 'green', bio-based crosslinker. The utilization of SFS, a by-product with no potential application, showed promising results after oxidizing it to a polyaldehyde. This valorizes the by-product from soy processing industry and reduces the waste. The presence of different sugars in SFS was found to be beneficial by not only providing multiple aldehyde groups but also different molecular lengths, increasing crosslinking efficiency. The higher crosslink density within the wool fiber improves its strength and modulus significantly. The room temperature extraction and oxidization process used in this study is also an energy efficient way of making a natural, bio-based crosslinker for protein-based polymers. The availability of SFS at very low cost and ease of oxidation reaction makes it scalable at commercial level. The method presented here can be easily extended for crosslinking other protein-based materials. The present research has shown that SFS, an agro-waste, can be oxidized for use as a 'green' crosslinker. The OSFS prepared in this study can easily replace currently used toxic crosslinkers such as glyoxal, and glutaraldehyde. Enhanced tensile properties of wool fibers can not only increase the efficiencies of wool fiber spinning and weaving by reducing breakages but can also reduce yarn and fabric defects. More importantly, stronger wool can allow spinning finer yarns from the same fibers, increasing their value significantly.

Example 10

A Soy Flour Derived Sugar-based 'Green' Crosslinker for Wool Fibers

Optimization of $NaIO_4$:SFS Molar Ratio.

Addition of oxidized soy flour sugars (OSFS) to soy flour (SF) shows an instantaneous color change due to Maillard reaction. FIG. 30 shows the effect of addition of OSFS with different molar ratios of $NaIO_4$:SFS from 0.5 to 2.5 on the color of SF. As seen in FIG. 30, the color of the SF changes from off-white to yellow-brown with the increase in the oxidation of soy flour sugars (SFS) from 0.5 to 2 after which it remains constant. $NaIO_4$:SF MR 2.5 showed maximum color change and thus was used to crosslink wool fibers. For the molar calculations, the molecular weight of SFS was assumed to be 342, which is the molecular weight of sucrose.

Optimization of $BaCl_2$:$NaIO_4$ molar ratio.

At the end of the oxidation of SFS, optimum amount of $BaCl_2$ was added to curb the oxidation reaction. When $BaCl_2$ is added to $NaIO_3$, they react to form barium iodate $Ba(IO_3)_2$ which is insoluble in water at lower temperatures. The reaction mixture was refrigerated to precipitate $Ba(IO_3)_2$. Different molar ratios of $BaCl_2$:$NaIO_4$ (0, 0.5, 1 and 1.5) were added to the reaction mixture and placed in the refrigerator for 1 h. As seen in FIG. 31, the parafilm on the beaker without $BaCl_2$ turns purple possibly due to the presence of free iodine fumes. With increase in the amount of $BaCl_2$ and the time in refrigerator, the purple color on the parafilm reduced. At MR 1.5, no purple color (no free iodine fumes) was observed and OSFS turned clear, indicating formation of $Ba(IO_3)_2$. The OSFS was then filtered to obtain OSFS. Thus, $BaCl_2$:$NaIO_4$ MR 1.5 was used to remove $NaIO_3$ from the reaction mixture.

REFERENCES

Citation of a reference herein shall not be construed as an admission that such reference is prior art to the present invention. All references cited herein are hereby incorporated by reference in their entirety. Below is a listing of various references cited herein by Reference ("Ref.") number:

(1) Chen, D.; Tan, L.; Liu, H.; Tang, F.; Hu, J.; Li, Y. Fabrication of Fast-Absorbing and Quick-Drying Wool Fabrics with Good Washing Durability. *Chem Sus Chem* 2010, 3 (9), 1031-1035.

(2) Chen, D.; Tan, L.; Liu, H.; Hu, J.; Li, Y.; Tang, F. Fabricating superhydrophilic wool fabrics. *Langmuir* 2009, 26 (7), 4675-4679.

(3) Johnson, N. A.; Russell, I. In *Advances in wool technology*. Elsevier: Woodhead publishing: England, 2008.

(4) Prins, M. Advances in wool spinning technology. In *Advances in Wool Technology*, Elsevier: Woodhead publishing, 2009; pp 86-105.

(5) Barani, H.; Calvimontes, A. Effects of oxygen plasma treatment on the physical and chemical properties of wool fiber surface. *Plasma Chem. Plasma P.* 2014, 34 (6), 1291-1302.

(6) Rahman, M. M.; Netravali, A. N. Green resin from forestry waste residue "Karanja (*Pongamia pinnata*) seed cake" for biobased composite structures. *ACS Sustain. Chem. Eng.* 2014, 2 (10), 2318-2328.

(7) Corfield, M.; Robson, A. The amino acid composition of wool. *Biochem. J.* 1955, 59 (1), 62.

(8) Di Modica, G.; Marzona, M. Cross-linking of wool keratin by bifunctional aldehydes. *Text. Res. J* 1971, 41 (8), 701-705.

(9) Song, K.; Xu, H.; Mu, B.; Xie, K.; Yang, Y. Non-toxic and clean crosslinking system for protein materials: Effect of extenders on crosslinking performance. *J. Clean. Prod.* 2017, 150, 214-223.

(10) Xu, H.; Song, K.; Mu, B.; Yang, Y. Green and Sustainable Technology for High-Efficiency and Low-Damage Manipulation of Densely Crosslinked Proteins. *ACS Omega* 2017, 2 (5), 1760-1768.

(11) Reddie, R.; Nicholls, C. Some reactions between wool and formaldehyde. *Text. Res. J.* 1971, 41 (10), 841-852.

(12) Mohsin, M.; Farooq, U.; Raza, Z. A.; Ahsan, M.; Afzal, A.; Nazir, A. Performance enhancement of wool fabric with environmentally-friendly bio-cross-linker. *J. Clean. Prod.* 2014, 68, 130-134.

(13) Milazzo, M.; Spina, F.; Cavallaro, S.; Bart, J. Sustainable soy biodiesel. *Renew. Sust. Energ. Rev.* 2013, 27, 806-852.

(14) Qiu, K.; Netravali, A. N. "Green" composites based on bacterial cellulose produced using novel low cost carbon source and soy protein resin. In *Recent Advances in Adhesion Science and Technology in Honor of Dr. Kash Mittal*, CRC Press: 2014.

(15) Ghosh Dastidar, T.; Netravali, A. N. A soy flour based thermoset resin without the use of any external crosslinker. *Green Chem.* 2013, 15 (11), 3243-3251.

(16) Duus, J. Ø.; Gotfredsen, C. H.; Bock, K. Carbohydrate structural determination by NMR spectroscopy: modern methods and limitations. *Chem. Rev.* 2000, 100 (12), 4589-4614.

(17) Fort, D. A.; Swatloski, R. P.; Moyna, P.; Rogers, R. D.; Moyna, G. Use of ionic liquids in the study of fruit ripening by high-resolution $^{13}C$ NMR spectroscopy: 'green' solvents meet green bananas. *Chem. Commun.* 2006, (7), 714-716.

(18) Kazalaki, A.; Misiak, M.; Spyros, A.; Dais, P. Identification and quantitative determination of carbohydrate molecules in Greek honey by employing 13 C NMR spectroscopy. *Anal. Methods* 2015, 7 (14), 5962-5972.

(19) Bubb, W. A. NMR spectroscopy in the study of carbohydrates: Characterizing the structural complexity. *Concept. Mag. Reson. A* 2003, 19 (1), 1-19.

(20) Barclay, T.; Ginic-Markovic, M.; Johnston, M. R.; Cooper, P.; Petrovsky, N. Observation of the keto tautomer of D-fructose in D2O using 1H NMR spectroscopy. *Carbohyd. Res.* 2012, 347 (1), 136-141.

(21) Jarrell, H. C.; Conway, T. F.; Moyna, P.; Smith, I. C. Manifestation of anomeric form, ring structure, and linkage in the $^{13}C$-NMR spectra of oligomers and polymers containing D-fructose: maltulose, isomaltulose, sucrose, leucrose, 1-kestose, nystose, inulin, and grass levan. *Carbohydrate Research* 1979, 76 (1), 45-57.

(22) Obendorf, R. L.; Sensenig, E. M.; Wu, J.; Ohashi, M.; O'Sullivan, T. E.; Kosina, S. M.; Schnebly, S. R. Soluble carbohydrates in mature soybean seed after feeding D-chiro-inositol, myo-inositol, or D-pinitol to stem-leaf-pod explants of low-raffinose, low-stachyose lines. *Plant Sci.* 2008, 175 (5), 650-655.

(23) Anjos, O.; Campos, M. G.; Ruiz, P. C.; Antunes, P. Application of FTIR-ATR spectroscopy to the quantification of sugar in honey. *Food Chem.* 2015, 169, 218-223.

(24) Lin, C.-A.; Ayvaz, H.; Rodriguez-Saona, L. E. Application of portable and handheld infrared spectrometers for determination of sucrose levels in infant cereals. *Food Anal. Methods* 2014, 7 (7), 1407-1414.

(25) Bureau, S.; Ruiz, D.; Reich, M.; Gouble, B.; Bertrand, D.; Audergon, J.-M.; Renard, C. M. Application of ATR-FTIR for a rapid and simultaneous determination of sugars and organic acids in apricot fruit. *Food Chem.* 2009, 115 (3), 1133-1140.

(26) Xu, H.; Canisag, H.; Mu, B.; Yang, Y. Robust and flexible films from 100% starch cross-linked by biobased disaccharide derivative. *ACS Sustain. Chem. Eng.* 2015, 3 (11), 2631-2639.

(27) Jalaja, K.; James, N. R. Electrospun gelatin nanofibers: a facile cross-linking approach using oxidized sucrose. *Int. J. Biol. Macromol.* 2015, 73, 270-278.

(28) Ghosh, B.; Jones, A. D. Profiling, characterization, and analysis of natural and synthetic acylsugars (sugar esters). *Anal. Methods* 2017, 9 (6), 892-905.

(29) Liu, P.; Xu, H.; Mi, X.; Xu, L.; Yang, Y. Oxidized Sucrose: A Potent and Biocompatible Crosslinker for Three-Dimensional Fibrous Protein Scaffolds. *Macromol. Mater. Eng.* 2015, 300 (4), 414-422.

(30) Xu, W.; Ke, G.; Wu, J.; Wang, X. Modification of wool fiber using steam explosion. *Eur. Polym. J.* 2006, 42 (9), 2168-2173.

(31) Yao, J.; Liu, Y.; Yang, S.; Liu, J. Characterization of Secondary Structure Transformation of Stretched and Slenderized Wool Fibers with FTIR Spectra. *J. Eng. Fiber. Fabr. (JEFF)* 2008, 3 (2).

(32) Rahman, M. M.; Netravali, A. N. Micro-fibrillated cellulose reinforced eco-friendly polymeric resin from non-edible 'Jatropha curcas' seed waste after biodiesel production. *RSC Adv.* 2016, 6 (52), 47101-47111.

(33) Lodha, P.; Netravali, A. N. Thermal and mechanical properties of environment-friendly 'green'plastics from stearic acid modified-soy protein isolate. *Ind. Crop. Prod.* 2005, 21 (1), 49-64.

(34) Chabba, S.; Matthews, G.; Netravali, A. N. 'Green' composites using cross-linked soy flour and flax yarns. *Green Chem.* 2005, 7 (8), 576-581.

(35) Nguyen, T.-H.; Lee, B.-T., Fabrication and characterization of cross-linked gelatin electro-spun nano-fibers. *J. Biomed. Sci. Eng.* 2010, 3 (12), 1117.

(36) Park, S.; Bae, D.; Rhee, K. Soy protein biopolymers cross-linked with glutaraldehyde. *J. Am. Oil Chem.' Soc.* 2000, 77 (8), 879-884.

(37) Rhim, J.-W.; Gennadios, A.; Weller, C. L.; Cezeirat, C.; Hanna, M. A. Soy protein isolate-dialdehyde starch films. *Ind. Crop. Prod.* 1998, 8 (3), 195-203.

(38) Happich, W.; Windus, W.; Naghski, J. Stabilization of wool by glutaraldehyde. *Text. Res. J.* 1965, 35 (9), 850-852.

(39) Song, F.; Tang, D.-L.; Wang, X.-L.; Wang, Y.-Z. Biodegradable soy protein isolate-based materials: a review. *Biomacromolecules* 2011, 12 (10), 3369-3380.

(40) Wang, L.-F.; Rhim, J.-W. Preparation and application of agar/alginate/collagen ternary blend functional food packaging films. *International journal of biological macromolecules* 2015, 80, 460-468.

(41) Bhat, R.; Karim, A. Towards producing novel fish gelatin films by combination treatments of ultraviolet radiation and sugars (ribose and lactose) as cross-linking agents. *J. Food Sci. Tech.* 2014, 51 (7), 1326-1333.

(42) Jiang, B.; Liu, Y.; Bhandari, B.; Zhou, W. Impact of caramelization on the glass transition temperature of several caramelized sugars. Part I: chemical analyses. *J. Agr. Food Chem.* 2008, 56 (13), 5138-5147.

(43) Feughelman, M. *Mechanical properties and structure of alpha-keratin fibres: wool, human hair and related fibres.* UNSW press: 1997.

(44) Popescu, C.; Wortmann, F.-J. Wool-structure, mechanical properties and technical products based on animal fibres. *Industrial Applications of Natural Fibres: Structure, Properties and Technical Applications*; John Wiley & Sons, 2010, 255-266.

(45) Hassan, M. M.; Schiermeister, L.; Staiger, M. P. Sustainable Production of Carbon Fiber: Effect of Cross-Linking in Wool Fiber on Carbon Yields and Morphologies of Derived Carbon Fiber. *ACS Sustain. Chem. Eng.* 2015, 3 (11), 2660-2668.

(46) Hossain, K. M. G.; González, M. D.; Juan, A. R.; Tzanov, T. Enzyme-mediated coupling of a bi-functional phenolic compound onto wool to enhance its physical, mechanical and functional properties. *Enzyme Microb. Tech.* 2010, 46 (3-4), 326-330.

(47) Mayo Jr, J.; Wetzel, E. Cut resistance and failure of high-performance single fibers. *Text. Res. J* 2014, 84 (12), 1233-1246.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method of crosslinking keratin-containing fibers, said method comprising:
   providing a crosslinking agent comprising an oxidized sugar mixture comprising a plurality of different oxidized sugars having at least two aldehyde groups, wherein the sugars are selected from the group consisting of monosaccharides, disaccharides, trisaccharides, and tetrasaccharides; and
   infiltrating a plurality of keratin-containing fibers with the crosslinking agent under conditions effective to cause protein molecules contained in the keratin-containing fibers to become crosslinked, thereby yielding a population of crosslinked keratin-containing fibers,
   wherein the protein molecules of the keratin-containing fibers comprise amine groups that react with the at least two aldehyde groups of the oxidized sugars to achieve the crosslinking of the protein molecules to yield the crosslinked keratin-containing fibers.

2. The method according to claim 1, wherein said infiltrating step is carried out at a temperature and for a length of time sufficient to yield crosslinked keratin-containing fibers having improved tensile properties selected from the group consisting of increased tensile strength and increased Young's modulus compared to the non-crosslinked keratin-containing fibers.

3. The method according to claim 2, wherein the increased tensile strength comprises an increase in tensile strength selected from the group consisting of at least 20 percent, at least 25 percent, at least 30 percent, and at least 35 percent.

4. The method according to claim 2, wherein the increased Young's modulus comprises an increase in Young's modulus selected from the group consisting of at least 20 percent, at least 25 percent, at least 30 percent, at least 35 percent, at least 40 percent, at least 45 percent, at least 50 percent, at least 55 percent, and at least 60 percent.

5. The method according to claim 2, wherein said temperature used in the infiltrating step is between about 130° C. and about 160° C. for a period of time of between about 15 minutes and 25 minutes.

6. The method according to claim 2, wherein the temperature is increased above room temperature by heating that is carried out by applying a source of heat during the infiltrating step, wherein the source of heat is selected from the group consisting of a flat iron, hot rollers, a hot plate, a curling iron, a hair dryer, an iron, a clothes dryer, and an oven.

7. The method according to claim 1 further comprising:
washing the population of keratin-containing fibers to remove residual crosslinking agent or to remove crosslinking agent adhering to the keratin-containing fibers, thereby substantially removing the crosslinking agent.

8. The method according to claim 1, wherein the keratin-containing fibers are human hair fibers.

9. The method according to claim 1, wherein the keratin-containing fibers are animal fibers selected from the group consisting of wool, alpaca, angora, fur, cashmere, mohair, and qiviut.

10. The method according to claim 1, wherein the keratin-containing fibers are animal fibers from animals selected from the group consisting of sheep, vicuna, alpaca, llama, muskox, goats, bison, camel, yak, horse, chinchilla, and rabbit.

11. The method according to claim 1, wherein the keratin-containing fibers are animal fibers having a form selected from the group consisting of raw fibers, yarns, felts, and woven or knitted fabrics.

12. The method according to claim 1, wherein the sugars are water soluble.

13. The method according to claim 1, wherein the oxidized sugar mixture comprises oxidized soy flour sugars (OSFS) having sugars selected from the group consisting of galactose, xylose, mannose, fructose, glucose, sucrose, raffinose, and stachyose.

14. The method according to claim 1, wherein the sugars have a ratio of aldehyde per saccharide unit selected from the group consisting of $\geq 1$, $>1$, $>1.5$, and $\geq 2$.

15. The method according to claim 1, wherein the crosslinking agent is prepared according to a method comprising the steps of:
providing a mixture of non-oxidized sugar molecules comprising a plurality of different sugars; and
reacting the non-oxidized sugar molecules with an oxidizing agent comprising sodium periodate ($NaIO_4$) to cause oxidation of the non-oxidized sugar molecules to yield a reaction mixture comprising an oxidized sugar mixture comprising a plurality of different oxidized sugars having at least two aldehyde groups, said oxidized sugar molecules corresponding to the crosslinking agent.

16. The method according to claim 15 further comprising: introducing barium chloride ($BaCl_2$) to the reaction mixture to inhibit further oxidation of the sugar molecules.

17. The method according to claim 15, wherein the crosslinking agent comprises an oxidized soy flour sugars (OSFS) mixture having a pH of about 3.

18. A method of making a crosslinking formulation for crosslinking keratin-containing fibers, said method comprising the steps of:
providing a mixture of non-oxidized sugar molecules comprising a plurality of different sugars; and
reacting the non-oxidized sugar molecules with an oxidizing agent comprising sodium periodate ($NaIO_4$) to cause oxidation of the non-oxidized sugar molecules to yield a crosslinking formulation comprising an oxidized sugar mixture comprising a plurality of different oxidized sugars having at least two aldehyde groups,
wherein the sugars are selected from the group consisting of monosaccharides, disaccharides, trisaccharides, and tetrasaccharides, and
wherein said mixture of oxidized sugars are crosslinking agents effective to react with amine groups of protein molecules contained in non-crosslinked keratin-containing fibers to yield a population of crosslinked keratin-containing fibers.

19. A crosslinking formulation produced according to the method of claim 18.

20. A method of treating keratin-containing fibers to improve their tensile properties, said method comprising the steps of:
providing a crosslinking formulation according to claim 19; and
treating a population of non-crosslinked keratin-containing fibers with the crosslinking formulation so as to yield a population of crosslinked keratin-containing fibers having improved tensile properties as compared to the population of non-crosslinked keratin-containing fibers, wherein the population of non-crosslinked keratin-containing fibers comprises non-crosslinked keratin-containing fibers having protein molecules having amine groups that react with the aldehyde groups of the different oxidized sugars of the crosslinking formulation,
wherein the sugars are selected from the group consisting of monosaccharides, disaccharides, trisaccharides, and tetrasaccharides, and
wherein the improved tensile properties are selected from the group consisting of increased tensile strength and increased Young's modulus compared to the non-crosslinked keratin-containing fibers.

21. The method according to claim 1, wherein the monosaccharides comprise 5 carbon sugars, 6 carbon sugars, or both 5 and 6 carbon sugars.

22. The method according to claim 18, wherein the monosaccharides comprise 5 carbon sugars, 6 carbon sugars, or both 5 and 6 carbon sugars.

23. The method according to claim 20, wherein the monosaccharides comprise 5 carbon sugars, 6 carbon sugars, or both 5 and 6 carbon sugars.

* * * * *